US009492068B2

(12) United States Patent
Papania et al.

(10) Patent No.: US 9,492,068 B2
(45) Date of Patent: Nov. 15, 2016

(54) NASAL AEROSOL DELIVERY SYSTEM

(75) Inventors: Mark J. Papania, Lilburn, GA (US); James J. Barry, Hanover, NH (US); Mark C. Bagley, Grafton, NH (US); Eric M. Friets, Norwich, VT (US); Darin A. Knaus, Norwich, VT (US)

(73) Assignees: THE UNITED STATES OF AMERICA, AS REPRESENTED BY THE SECRETARY, DEPARTMENT OF HEALTH AND HUMAN SERVICES, Washington, DC (US); CREARE LLC, Hanover, NH (US)

( * ) Notice: Subject to any disclaimer, the term of this patent is extended or adjusted under 35 U.S.C. 154(b) by 867 days.

(21) Appl. No.: 13/701,992

(22) PCT Filed: Jun. 3, 2011

(86) PCT No.: PCT/US2011/039020
§ 371 (c)(1),
(2), (4) Date: Dec. 4, 2012

(87) PCT Pub. No.: WO2011/153406
PCT Pub. Date: Dec. 8, 2011

(65) Prior Publication Data

US 2013/0072755 A1 Mar. 21, 2013

Related U.S. Application Data

(60) Provisional application No. 61/351,745, filed on Jun. 4, 2010.

(51) Int. Cl.
*A61M 15/08* (2006.01)
*A61B 1/233* (2006.01)
(Continued)

(52) U.S. Cl.
CPC ................. *A61B 1/233* (2013.01); *A61B 1/04* (2013.01); *A61B 1/06* (2013.01); *A61M 11/00* (2013.01);

(Continued)

(58) Field of Classification Search
CPC ........... A61M 15/08; A61M 15/0098; A61M 15/0091
See application file for complete search history.

(56) References Cited

U.S. PATENT DOCUMENTS 6,102,036 A 8/2000 Slutsky et al.
6,152,130 A 11/2000 Abrams et al.
(Continued)

FOREIGN PATENT DOCUMENTS

EP 0 739 654 10/1996
EP 2 119 465 11/2009
(Continued)

OTHER PUBLICATIONS

International Search Report and the Written Opinion of the International Searching Authority from International Application No. PCT/US2011/039020 dated Jan. 16, 2012.

*Primary Examiner* — Aarti B Berdichevsky
(74) *Attorney, Agent, or Firm* — Klarquist Sparkman, LLP

(57) ABSTRACT

A nasal delivery device can include a nasal prong and an activation member. The nasal prong can comprises an opening at a top and bottom portion of the prong to allow for the passage of an aerosolized treatment agent through the nasal prong. The activation member can be positioned on the nasal delivery device at a location that is spaced apart from the subject's oral cavity when the nasal prong is received into the nostril of the subject. The activation member can be configured to detect a desired exhalation state of the subject and upon detection of the desired exhalation state, the activation member activates the delivery of the aerosolized treatment agent.

41 Claims, 15 Drawing Sheets

(51) Int. Cl.

| | |
|---|---|
| ***A61M 11/00*** | (2006.01) |
| ***A61B 1/04*** | (2006.01) |
| ***A61B 1/06*** | (2006.01) |
| ***A61M 15/00*** | (2006.01) |
| *A61M 16/04* | (2006.01) |
| *A61M 16/00* | (2006.01) |

(52) U.S. Cl.

CPC .......... *A61M 11/005* (2013.01); *A61M 11/007* (2014.02); *A61M 15/0098* (2014.02); *A61M 15/08* (2013.01); *A61M 16/0488* (2013.01); *A61M 2016/0024* (2013.01); *A61M 2016/0042* (2013.01); *A61M 2205/3365* (2013.01); *A61M 2205/3375* (2013.01); *A61M 2205/43* (2013.01); *A61M 2205/502* (2013.01); *A61M 2205/581* (2013.01); *A61M 2205/6036* (2013.01); *A61M 2205/6054* (2013.01); *A61M 2205/6063* (2013.01)

(56) References Cited

U.S. PATENT DOCUMENTS

| | | | | |
|---|---|---|---|---|
| 6,637,432 | B2 | 10/2003 | Wakefield et al. | |
| 7,219,664 | B2 | 5/2007 | Ruckdeschel et al. | |
| 7,225,807 | B2 | 6/2007 | Papania et al. | |
| 7,779,830 | B2 | 8/2010 | Koerner et al. | |
| 7,854,227 | B2 * | 12/2010 | Djupesland ....... | A61M 15/0086 128/203.15 |
| 8,910,629 | B2 * | 12/2014 | Djupesland ....... | A61M 15/0028 128/200.21 |
| 2002/0020408 | A1 | 2/2002 | Knauer | |
| 2003/0000524 | A1 | 1/2003 | Anderson et al. | |
| 2004/0228208 | A1 | 11/2004 | Papania et al. | |
| 2005/0028812 | A1 * | 2/2005 | Djupesland ....... | A61M 15/0091 128/200.21 |
| 2006/0096589 | A1 * | 5/2006 | Djupesland ....... | A61M 15/0086 128/200.14 |
| 2007/0039614 | A1 | 2/2007 | Djupesland | |
| 2007/0125371 | A1 * | 6/2007 | Djupesland ........... | A61M 15/00 128/200.14 |
| 2007/0186927 | A1 * | 8/2007 | Djupesland ........... | A61M 15/00 128/203.15 |
| 2009/0223513 | A1 | 9/2009 | Papania et al. | |
| 2010/0242959 | A1 * | 9/2010 | Djupesland ....... | A61M 15/0028 128/203.15 |
| 2011/0120456 | A1 * | 5/2011 | Immel ............... | A61M 15/0085 128/200.23 |
| 2015/0136132 | A1 * | 5/2015 | Papania ............ | A61M 15/0028 128/203.15 |
| 2016/0058960 | A1 * | 3/2016 | Papania ................ | A61M 15/08 600/103 |

FOREIGN PATENT DOCUMENTS

| | | |
|---|---|---|
| WO | WO 00/50111 | 8/2000 |
| WO | WO 01/41849 | 6/2001 |
| WO | WO 02/100468 | 12/2002 |
| WO | WO 03/090812 | 11/2003 |
| WO | WO 2007/101438 | 9/2007 |

* cited by examiner

Fig. 29B
Fig. 29A
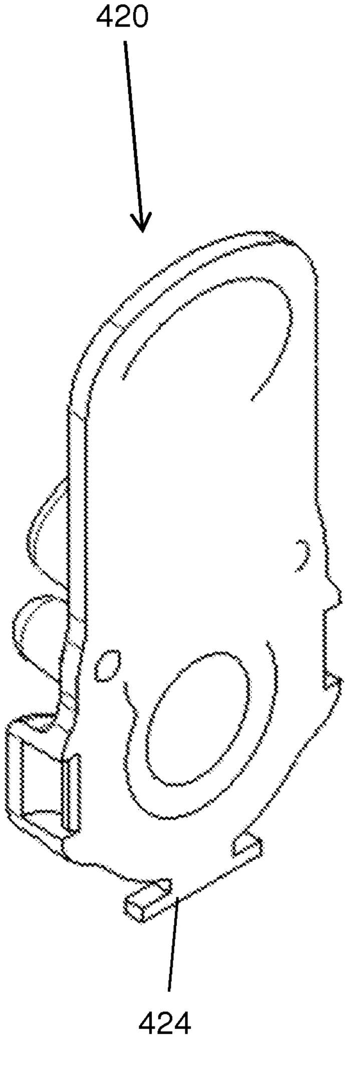
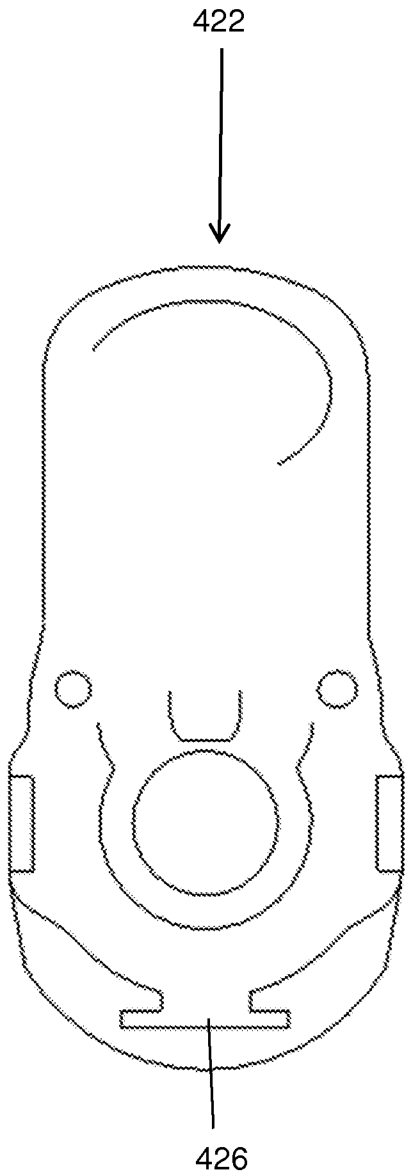

NASAL AEROSOL DELIVERY SYSTEM

CROSS REFERENCE TO RELATED APPLICATIONS

This is the U.S. National Stage of International Application No. PCT/US2011/039020, filed Jun. 3, 2011, which was published in English under PCT Article 21(2), which in turn claims the benefit of U.S. Provisional Application No. 61/351,745, filed Jun. 4, 2010. The provisional application is incorporated herein in its entirety.

FIELD

The present disclosure is directed to methods and apparatuses for intranasal delivery of a substance to a subject.

BACKGROUND

Various devices have been developed to provide for the nasal delivery of treatment agents, such as medications or vaccines, to a subject. In the delivery of some treatment agents, such as vaccines, it is desirable to direct the treatment agent to the nasal mucosal passages while, at the same time, minimizing deposition of the treatment agent in the lower respiratory tract. However, conventional nasal delivery devices generally exhibit a number of drawbacks.

Such drawbacks can include, for example, a requirement that a portion of the device directly contact the subject's mouth. If the delivery device directly contacts the mouth of the subject, the device can become contaminated and it cannot be used with other subjects unless certain procedures or steps are taken to sterilize the device after use. Other drawbacks of conventional delivery devices can include the failure to deliver the dosage at the right time, such as during an exhalation or while a subject is holding his or her breath. In addition, conventional delivery devices are difficult to aim, causing misalignment with the nasal passages of the subject's nose and reducing the amount of treatment agent that is delivered at the desired treatment areas in the nose.

SUMMARY

In one embodiment, a nasal delivery device is provided for delivering an aerosolized treatment agent to a subject. The device comprises a nasal prong and an activation member. The nasal prong can comprise an opening at a top and bottom portion of the prong to allow for the passage of the aerosolized treatment agent through the nasal prong, and at least a portion of the nasal prong can be configured to be received into a nostril of the subject. The activation member can be configured to detect a desired exhalation state of the subject. The activation member can be positioned on the nasal delivery device at a location that is spaced apart from the subject's oral cavity when the nasal prong is received into the nostril of the subject. The activation member activates the delivery of the aerosolized treatment agent through the nasal prong upon detecting the desired exhalation state of the subject.

In specific implementations, the desired exhalation state is an oral exhalation and the activation member is a microphone configured to detect a sound generated by air flow associated with the oral exhalation of the subject. In other specific implementations, a sound generating member can be provided that generates a sound upon exposure to air flow associated with the oral exhalation. The sound generating member can be, for example, a screen or whistle.

In specific implementations, the device can also comprise a deflector configured to deflect air flow generated by an oral exhalation of the subject towards the activation member. The deflector can include one or more walls that at least partially surround the activation member.

In specific implementations, the desired exhalation state is an oral exhalation and the activation member comprises a rotatable member that rotates upon exposure to the oral exhalation of the subject. In other specific implementations, an air flow source can be provided to direct air through the nasal prong to increase the air flow speed of the aerosolized treatment agent through the nasal prong.

In specific implementations, the device can also comprise a nebulizing device having a motion transmitting member and a receiving area adjacent the motion transmitting member of the nebulizing device for receiving a disposable aerosolizing element. The disposable aerosolizing element can comprise a housing that contains a treatment agent.

In specific implementations, the device can also include an alignment device. The alignment device can have a light source that directs light into the nostril of the subject to facilitate alignment of a delivery axis of the aerosolized treatment agent with a nasal airway of the subject. In other specific implementations, the alignment device can include a light detector that is generally collinearly aligned with the light source, and the light detector can be configured to detect the amount of light reflected from a surface in the subject's nasal airway.

In specific implementations, the alignment device can comprise an optical device generally collinearly aligned with the delivery axis of the aerosolized treatment agent to provide a view into the nostril of the patient to facilitate alignment of the delivery axis of the aerosolized treatment agent with the nasal airway of the subject. The alignment device can comprise an optical eyepiece for viewing into the nostril of the patient and/or a display screen for displaying an image of a view into the nostril of the patient.

In another embodiment, another nasal delivery device is provided for delivering an aerosolized treatment agent to a subject. The device comprises a nebulizing device and a remote activation member. The nebulizing device can have an aerosolizing mode and a non-aerosolizing mode. The remote activation member can be configured to detect an oral exhalation of the subject without coming into direct contact with the subject, with the remote activation member generating an activation signal to cause the nebulizing device to switch from the non-aerosolizing mode to the aerosolizing mode.

In specific implementations, the nebulizing device can comprise a motion transmitting member configured to transmit an oscillatory force in the aerosolizing mode. The force can be transmitted to a surface of a disposable aerosolizing device that is received in the nasal delivery device. The disposable aerosolizing device can contain a treatment agent.

In specific implementations, a dose timing switch can be provided that adjusts a length of time that the nebulizing device is in the aerosolizing mode after generation of the activation signal.

In specific implementations, the device includes a disposable aerosolizing element that comprises a housing that contains a treatment agent. The disposable aerosolizing element can comprise a storage reservoir, a dispensing reservoir, and a temporary barrier restricting flow between the external and dispensing reservoirs. The temporary barrier can be removable upon application of a physical force to the storage reservoir.

In specific implementations, the remote activation member can comprise a microphone. A deflector can also be provided to deflect air flow generated by the oral exhalation of the subject towards the activation member. The deflector can comprise one or more walls that at least partially surround the activation member.

In specific implementations, the aerosolized treatment agent is configured to be directed into a nostril of the subject generally along a predetermined delivery axis, wherein the nasal delivery device further comprises an alignment device to generally align a nasal airway of the subject with the predetermined delivery axis. The alignment device can include a light source and a light detector that are generally collinearly aligned, with the light detector being configured to detect the amount of light reflected from a surface in the subject's nasal airway.

In specific implementations, the alignment device can comprise an optical device that is generally collinearly aligned with the delivery axis of the aerosolized treatment agent to provide a view into the nostril of the patient to facilitate alignment of the delivery axis of the aerosolized treatment agent with the nasal airway of the subject. The alignment device can also comprise an optical eyepiece for viewing into the nostril of the patient or a display screen for displaying an image of the nostril of the patient.

In another embodiment, a method is provided for directing an aerosolized treatment agent into a nostril of a subject. The method comprises positioning a nasal prong of a nasal delivery device at least partially within a nostril of the subject; detecting a desired exhalation state of the subject with a detection device positioned at a location remote from the oral cavity of the subject such that the detection device does not directly contact the subject; activating a nebulizing device to cause the aerosolization of a treatment agent upon detection of the desired exhalation state; and delivering the aerosolized treatment agent through the nasal prong and into the nostril of the subject.

In specific implementations, the desired exhalation state of the subject is an oral exhalation. In other specific implementations, the act of detecting the oral exhalation comprises detecting a sound generated by air flow associated with the oral exhalation of the subject using a microphone. In other specific implementations, the method further includes deflecting air from the oral exhalation towards the microphone.

In specific implementations, the act of activating the nebulizing device comprises transmitting an oscillatory force to a surface of a disposable aerosolizing device that contains the treatment agent. In other specific implementations, the method further comprises directing air from an air flow source through the nasal prong to increase the air flow speed of the aerosolized treatment agent through the nasal prong.

In other specific implementations, the method further comprises aligning a delivery axis of the aerosolized treatment agent with a nasal airway of the subject. The act of aligning the delivery device can comprise directing light into the nostril of the subject and detecting light reflected from a surface in the subject's nostril. In other specific implementations, the act of aligning the delivery device comprises directing light into the nostril of the subject and viewing the inside of the nostril using an optical device. The act of viewing the inside of the nostril using an optical device can comprise displaying an image of the nostril on a display screen.

The alignment devices and methods of aligning the delivery axis of the aerosolized treatment agent with a nasal airway can be used independently of the remote activation member. Thus, in another embodiment, a nasal delivery device for delivering an aerosolized treatment agent to a subject includes a nasal prong and an alignment device. The nasal prong has an opening at a top and bottom portion of the prong to allow for the passage of the aerosolized treatment agent through the nasal prong. A longitudinal axis of the nasal prong generally defines a delivery axis of the aerosolized treatment agent, and at least a portion of the nasal prong can be received into a nostril of the subject. The alignment device is configured to facilitate aligning the delivery axis of the aerosolized treatment agent with a nasal airway of the subject.

In specific implementations, the alignment device further comprises a light source and a light detector that are generally coaxially aligned. The light detector can detect an amount of light reflected from a surface in the subject's nostril. Upon detection of an amount of reflected light that is greater than a predetermined amount, the alignment device can indicate that the delivery axis of the aerosolized treatment agent is not aligned with the nasal airway, and upon detection of an amount of reflected light that is less than a predetermined amount, the alignment device can indicate that the delivery axis of the aerosolized treatment agent is aligned with the nasal airway.

In specific implementations, the alignment device can comprise a light source that directs light into the nostril of the subject to facilitate alignment of the delivery axis of the aerosolized treatment agent with the nasal airway of the subject. The alignment device can comprise an optical device that is generally collinearly aligned with the delivery axis of the aerosolized treatment agent to provide a view into the nostril of the patient to facilitate alignment of the delivery axis of the aerosolized treatment agent with the nasal airway of the subject.

In specific implementations, the optical device can comprise an eyepiece at one end and a wide angle lens at another end. In other specific implementations, the eyepiece and the lens are not collinearly arranged. In other specific implementations, the optical device comprises a display screen and a camera. In yet other specific implementations, the camera can be positioned to receive images of an interior of the nostril through the nasal prong. The display screen can be integrally formed with the nasal delivery device.

In another embodiment, a nasal delivery device for delivering an aerosolized treatment agent to a subject is provided. The device includes a nebulizing device and an alignment device. The nebulizing device can be configured to aerosolize a treatment agent and deliver the aerosolized treatment agent along a predetermined delivery axis into a nostril of a subject. The alignment device is configured to align the delivery axis of the aerosolized treatment agent with a nasal airway of the subject.

In specific implementations, the delivery axis of the aerosolized treatment agent is at least partly defined by a nasal prong through which the aerosolized treatment agent is delivered. In other specific implementations, the alignment device can comprise a light source and a light detector that are generally coaxially aligned, and the light detector can detect an amount of light reflected from a surface in the subject's nostril to determine whether the delivery axis of the aerosolized treatment agent is aligned with the nasal airway.

In specific implementations, the alignment device can comprise a light source that directs light into the nostril of the subject to facilitate alignment of the delivery axis of the aerosolized treatment agent with the nasal airway of the subject. The alignment device can comprise an optical device generally coaxially aligned with the delivery axis of the aerosolized treatment agent to provide a view into the nostril of the patient to facilitate alignment of the delivery axis of the aerosolized treatment agent with the nasal airway of the subject. The optical device can also comprise a display screen and a camera. The camera can be positioned to receive images of an interior of the nostril through the nasal prong. The display screen can be integrally formed with the nasal delivery device.

In specific implementations, the nebulizing device can comprise a motion transmitting member configured to transmit an oscillatory force in the aerosolizing mode, with the force being transmitted to a surface of a disposable aerosolizing device that is received in the nasal delivery device. The disposable aerosolizing device can contain a treatment agent. The disposable aerosolizing element can also comprise a storage reservoir, a dispensing reservoir, and a temporary barrier restricting flow between the external and dispensing reservoirs. The temporary barrier can be removable upon application of a physical force to the storage reservoir. The disposable aerosolizing element can also comprise an optical port, and an optical device can be positioned into or adjacent the optical port to receive an unobstructed view through the disposable aerosolizing element.

In another embodiment, a method of aligning a delivery axis of an aerosolized treatment agent with a nasal airway of a subject is provided. The method can comprise positioning a portion of a nasal delivery device at least partly into a nostril of a subject; illuminating an interior area of the nostril with light; and determining whether a delivery axis of the aerosolized treatment agent is aligned with the nasal airway of a subject.

In specific implementations, the light directed into the nostril is generally directed along the delivery axis of the aerosolized treatment agent. In addition, the act of determining whether the delivery axis is aligned with the nasal airway comprises detecting an amount of light reflected from an inner surface of the nostril; determining whether the amount of reflected light is greater than or less than a predetermined amount; and indicating that the delivery axis of the aerosolized treatment agent is not aligned with the nasal airway if the amount of reflected light is greater than the predetermined amount or indicating that the delivery axis of the aerosolized treatment agent is aligned with the nasal airway if the amount of reflected light is less than the predetermined amount.

In specific implementations, the act of determining whether the delivery axis is aligned with the nasal airway comprises observing the illuminated interior area of the nostril using an optical device. In other specific implementations, the act of determining whether the delivery axis is aligned with the nasal airway comprises positioning a camera generally along the delivery axis of the aerosolized treatment agent to view the illuminated interior area; displaying an image captured by the camera on a display screen; and observing the image to determine whether the delivery axis of the aerosolized treatment agent is aligned with the nasal airway. In other specific implementations, upon observing that the delivery axis of the aerosolized treatment is not aligned with the nasal airway, the method further comprises the act of adjusting the orientation of the delivery axis of the aerosolized treatment agent.

The foregoing and other objects, features, and advantages of the invention will become more apparent from the following detailed description, which proceeds with reference to the accompanying figures.

BRIEF DESCRIPTION OF THE DRAWINGS

FIGS. 29A and 29B illustrate a mechanical recognition system whereby mechanical features, such as the shape of a disposable aerosolizing element housing, operate to help the delivery device identify and/or recognize the disposable aerosolizing element.

DETAILED DESCRIPTION

Figure 1A:
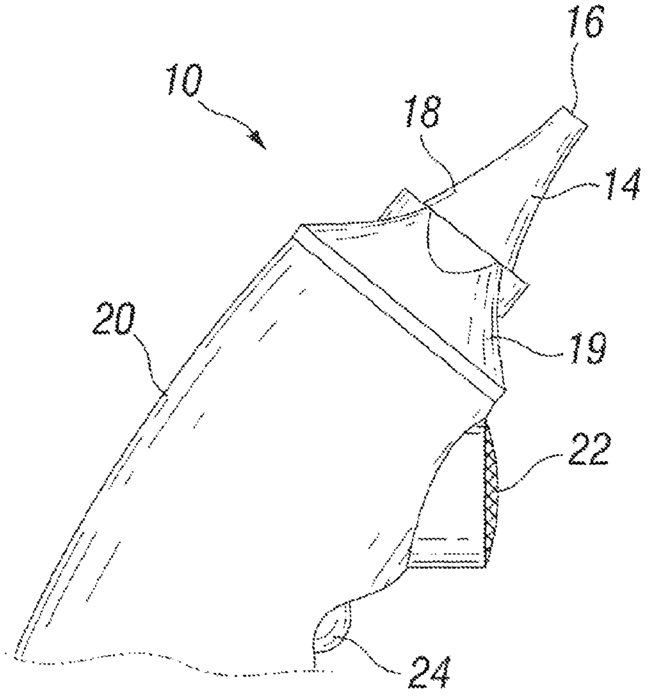
FIG. 1A is a partial side view of a nasal delivery device with a remote activation member.

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

Treatment agents, as used herein, comprise agents that can be administered to living organisms for an effect in the treated organism. Such agents include live and killed organisms for vaccination, immunogens, immune activators or suppressors, chemotherapeutics, pharmaceuticals, nucleic acids, insulin, hormones, antibodies and fragments thereof, receptors, proteins, carbohydrates, fats, nutrients, anesthetics, narcotics, and pain relievers.

Exemplary methods of the present disclosure comprise delivery of agents such as vaccine compositions. Certain methods of the present disclosure comprise delivery of vaccine compositions via aerosol administration. The present disclosure contemplates the use of any vaccine composition or other treatment agents that can be delivered via aerosol administration. Particularly preferred vaccination compositions are those for measles, mumps and rubella. Such compositions may comprise measles vaccine, mumps vaccine, rubella vaccine and combinations and mixtures such as measles and mumps, rubella and mumps, measles and rubella, and measles, mumps and rubella. Other particularly preferred vaccine compositions are those for influenza. Such compositions may comprise live virus vaccines, inactivated virus vaccines, and virus-like particle vaccines. The vaccines further comprise pharmaceutical or formulation components such as those known in the art, including, but not limited to, diluents, compounding agents, surfactants, and agents to maintain sterility.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Needles and syringes have posed a variety of problems for patients and medical personnel who administer agents to the patients, including injection safety, needle stick injury, disposal problems, transmission of blood borne diseases, and needle shortages during mass vaccination campaigns. The replacement of needles and syringes as the primary delivery vehicle for agents has the potential for tremendous cost savings, increased safety and reduction of biomedical wastes.

Aerosol delivery of agents avoids many of the foregoing drawbacks of injection. However, much of the equipment currently used for aerosol delivery is cumbersome or otherwise inconvenient and, therefore, it has not been widely employed for many treatment methods. For example, although nebulizers are commonly used in hospitals for aerosol delivery of agents in the treatment of respiratory diseases, they are not widely used outside of hospitals because of their size and/or difficulty of use. In practice, a nebulizer uses compressed gases to convert a solution of the agent into fine droplets. The droplets are administered to the patient through an air stream that the patient breathes inwardly through a mouthpiece or mask. As the patient breathes, the agent is delivered to the patient's lungs and absorbed therein. Typically, nebulizers rely upon an external compressed gas source to convert a solution of the agent into fine droplets. As a result of the need for an external source of compressed gas, nebulizers tend to be bulky and difficult to move. Further, the effectiveness of a nebulizer depends upon proper inhalation by the patient, which can be difficult to monitor and to teach to the patient. In addition, most nebulizers are designed as single-patient devices and are thus inappropriate for use with multiple patients, as can be desirable for administration of vaccines.

The following devices and methods provide an effective tool for delivering treatment agents without the difficulties associated with bulky, compressed gas nebulizers. In addition, the following devices and methods provide effective ways to deliver treatment agents accurately and effectively.

Figure 1B:
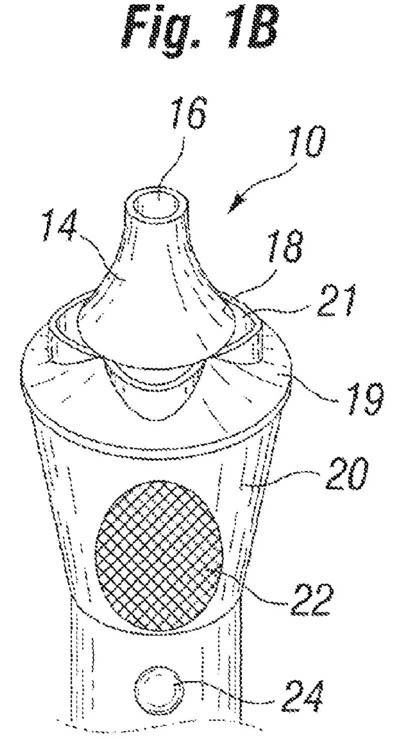
FIG. 1B is a partial front view of the nasal delivery device of FIG. 1A.

FIGS. 1A and 1B illustrate a first embodiment of a nasal delivery device 10. Nasal delivery device 10 comprises an extending portion (nasal prong) 14 that is sized to be received at least partly within one of the two nares (nostrils) of a subject's nose. Nasal prong 14 at least partially extends into or within a nostril if any portion of nasal prong 14 breaks a plane defined by the portion of the nose that surrounds a nostril opening. Nasal prong 14 includes an opening 16 at one end to allow for the delivery of a treatment agent from the delivery device 10 to the subject's nasal passages. Nasal prong 14 can be configured to taper from a wider portion 18 to the end with opening 16. Nasal prong 14 can be coupled to a base member 20, which can comprise, for example, a nebulizing device as discussed in more detail below. Nasal prong 14 can include a connecting portion 19 which attaches to base member 20. Nasal prong 14 can have ducts or openings 21 that allow ambient air to enter into nasal prong 14 to facilitate air flow through nasal prong 14 during delivery of the treatment agent. Prior to delivery to the nasal passage of a patient, the treatment agent can be stored in a storage member or device, such as a disposable aerosolizing element as described in more detail below.

The soft palate or velum is the soft tissue in the back of the roof of the oral cavity (e.g., mouth) that separates the nasal and oral cavities from one another. The velum is movable within the mouth to close the nasal cavities and passageways from the oral cavity when there is a positive pressure within the mouth, such as when a subject swallows, holds their breath, or forcefully exhales through the mouth. In contrast, when a subject inhales, the velum opens, allowing flow between the oral and nasal cavities. Embodiments disclosed herein describe various apparatuses and methods for automatically actuating the intranasal delivery of treatment agents to a subject based on a respiratory flow of the subject and, in particular, allow for effective delivery of the treatment agent when the patient is exhaling or holding their breath.

If a treatment agent is delivered into the nasal passageways while a subject is inhaling, the treatment agent can be inhaled by the subject into the lower respiratory tract, causing the treatment agent to miss the targeted location. Thus, by actuating the delivery of the treatment agent when the subject is not experiencing an inhalation, such as during an exhalation or when the subject is holding his or her breath, the delivery of the treatment agent into the nasal mucosal passageways can be maximized and the delivery of the treatment agent into the lower respiratory tract can be minimized. Although the velum can partially or fully close during exhalation or breathhold, the directing of the treatment agents in the following embodiments does not mandate such closure. Instead, the minimization of the delivery of the treatment agent into the lower respiratory tract relies largely on the avoidance of providing air flow through the nasal passageway into the lower respiratory tract, such as is provided when the subject inhales through his or her nose.

Referring again to FIGS. 1A and 1B, an activation member 22 can be positioned on a side of base member 20. Activation member 22 is desirably a remote member that is spaced apart from the oral cavity of the subject. By spacing activation member 22 away from the subject, activation member 22 can actuate the deployment of the treatment agent through nasal prong 14 and into one of the nostrils of the subject without directly contacting the subject. As described in various embodiments below, an activation member that is actuated by exhalation flow can be beneficial in that the initiation of delivery of the treatment agent occurs during exhalation, which can prevent or substantially restrict the delivery of the treatment agent into the trachea and lower airways.

Activation member is preferably located or positioned external to the subject's oral cavity (mouth) so that no portion of the activation member is received within or contacts the subject's mouth at any time. Thus, concerns about cross-contamination of the activation member caused by using the device with different subjects are reduced and/or substantially eliminated.

Activation member 22 can comprise a microphone that is configured to detect flow noise or sound that is generated by an oral exhalation. Activation member 22 can be configured to activate the delivery of the treatment agent upon detecting an exhalation of a certain sound intensity. Accordingly, activation member 22 can be configured so that an exhalation that is too soft or gentle will not trigger the delivery of the treatment agent. Preferably, activation member 22 is configured to actuate the delivery of the treatment agent upon detecting a sound level that falls within a range that is representative of a gentle exhalation by the subject. Thus, if desired, activation member 22 can be configured so that it will not trigger delivery of the treatment agent if the exhalation is too forceful.

The microphone can be a highly-directional microphone in order to eliminate or reduce the effects of noise generated from events other than exhalation of the subject. In addition, as shown in FIG. 1A, the microphone can be positioned below nasal prong 14 in an orientation directed towards the subject's mouth when the extending portion is positioned adjacent or within a naris for delivery of the treatment agent, so that the microphone will be positioned to generally receive only sounds emanating from the oral region of the subject.

Figure 2:
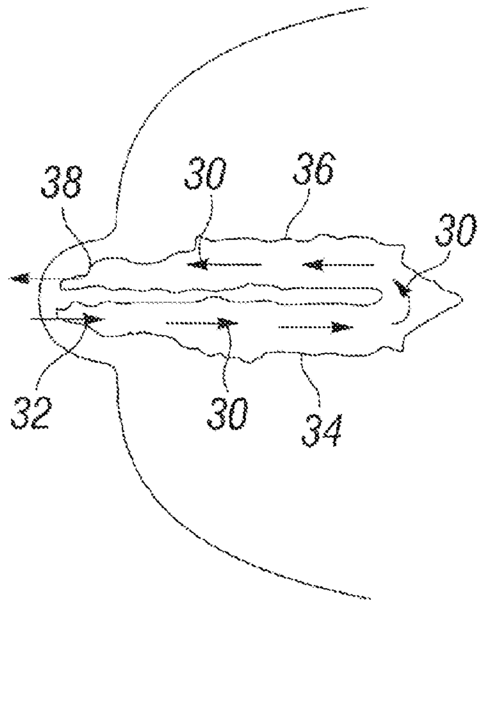
FIG. 2 is a schematic view of the delivery of a treatment agent through a single naris of a subject.

When activation member 22 is triggered, delivery device 10 delivers an aerosol plume or spray containing the treatment agent to one naris. The subject's velum can remain open during the administration of the treatment agent; however, closure of the subject's velum is acceptable if it occurs. Because the subject's velum can remain open, some exhalation may occur via the nasal passages. FIG. 2 illustrates the delivery of an aerosolized treatment agent 30 into a first naris 32 and through one side 34 of the nasal cavity. Upon reaching the posterior region of the nasal cavity, the aerosolized treatment agent can cross over into the other side 36 of the nasal cavity. Most of the agent 30 is deposited in the nasal cavity, although a small amount can ultimately exit through the other naris 38.

As shown in FIGS. 1A and 1B, activation member 22 is preferably spaced apart from the nasal and oral cavities of the subject at all times during operation of nasal delivery device 10. Because no part of the activation member (e.g., microphone) is in direct physical contact with the subject, the risk of cross-contamination between subjects is eliminated or at least greatly reduced.

If desired, a trigger switch or button 24 can be provided on device 10 to activate the delivery of the aerosolized treatment agent or to ready the device for delivery of a treatment reagent if a remote activation member is provided. Thus, to operate device 10, switch 24 can be depressed to turn on activation member 22 and device 10 can be readied for deployment of the treatment agent upon activation of remote activation member 22. Switch 24 can be an on/off type switch, or it can be a switch 24 that must be held in a depressed state in order to maintain device 10 in the "on"

state. If desired, these switches can be "ready" switches that are operable by the patient immediately prior to starting their exhalation to reduce the likelihood for a "false positive" detection of a patient's state or condition by the remote activation member.

Device 10 can include a disposable aerosolizing element positioned adjacent to and/or at least partially within nasal prong 14 to facilitate delivery of a treatment agent to a subject. The disposable aerosolizing element can be a single dose element that contains the treatment agent, such as the disk-shaped disposable aerosolizing element 50 shown in FIG. 3. Device 10 can include a nebulizing device or element that functions to aerosolize the treatment agent dose for delivery through opening 16 of nasal prong 14. Various disposable aerosolizing elements and nebulizing devices can be utilized in connection with device 10. For example, the various aerosol delivery systems shown and described in U.S. Pat. No. 7,225,807 and U.S. Patent Publication No. 2009/0223513 can be used in connection with the activation members described herein. The entire disclosures of U.S. Pat. No. 7,225,807 and U.S. Patent Publication No. 2009/0223513 are incorporated herein by reference.

Figure 3:
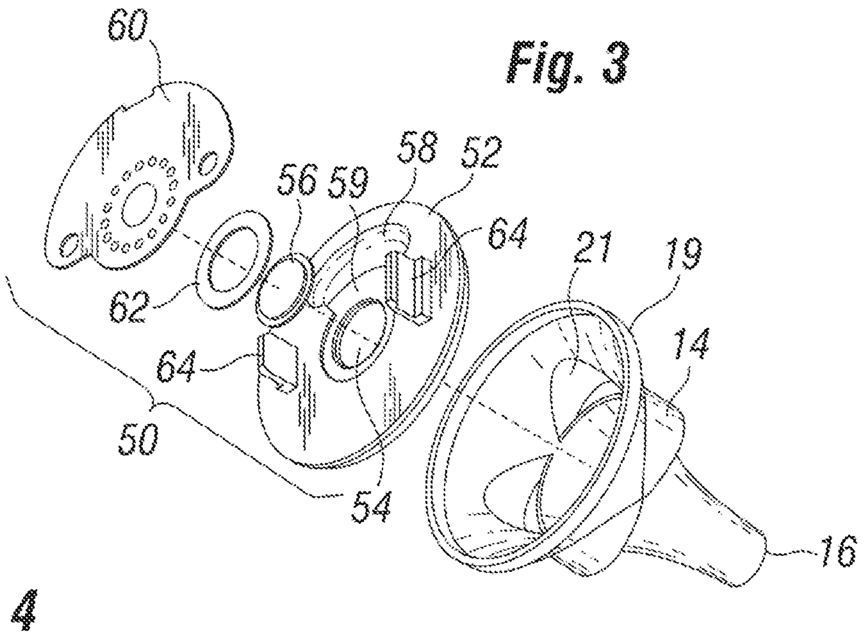
FIG. 3 is an exploded view of a disposable aerosolizing element and a nasal prong.

FIG. 3 illustrates a disposable aerosolizing element 50 that can be received and positioned adjacent nasal prong 14 to deliver a treatment agent to one or more nostrils of a subject. Disposable aerosolizing element 50 can comprise a housing 52 with an opening 54 that is at least partially covered by a mesh or other porous element 56. The mesh can comprise an electroformed metal foil that has a plurality of fluid ejection orifices through which the treatment agent can be delivered in an aerosol form. Meshes can also be fabricated of other materials and by other means, including, for example, various machining or molding processes. Housing 52 also preferably includes a reservoir 58 for receiving and storing the treatment agent prior to aerosolization and a fluid feed channel 59 to allow the treatment agent to flow from the reservoir 58 to an area adjacent mesh element 56 for aerosolization.

A backing or end member 60 can be positioned over reservoir 58 and/or mesh element 56 to seal the rear portion of disposable aerosolizing element 50 and enclose reservoir 58 and the fluid feed channels, thereby containing the treatment agent. Backing member 60 can comprise, for example, a backing film. If desired, backing member 60 can have a dimpled pattern to facilitate the establishment of the fluid-filled gap between backing member 60 and mesh element 56 for improved delivery of the aerosolized treatment agent.

Mesh element 56 can be secured to housing 52 over opening 54 using any suitable securement means, such as a tape ring 62. As described in more detail below, housing 52 can be secured to a nebulizing device so that the nebulizing device is positioned adjacent backing member 60. In one embodiment, one or more tab members 64 can extend from a surface of the housing 52 to facilitate the securement of the housing 52 to the nebulizing device.

Figure 4:
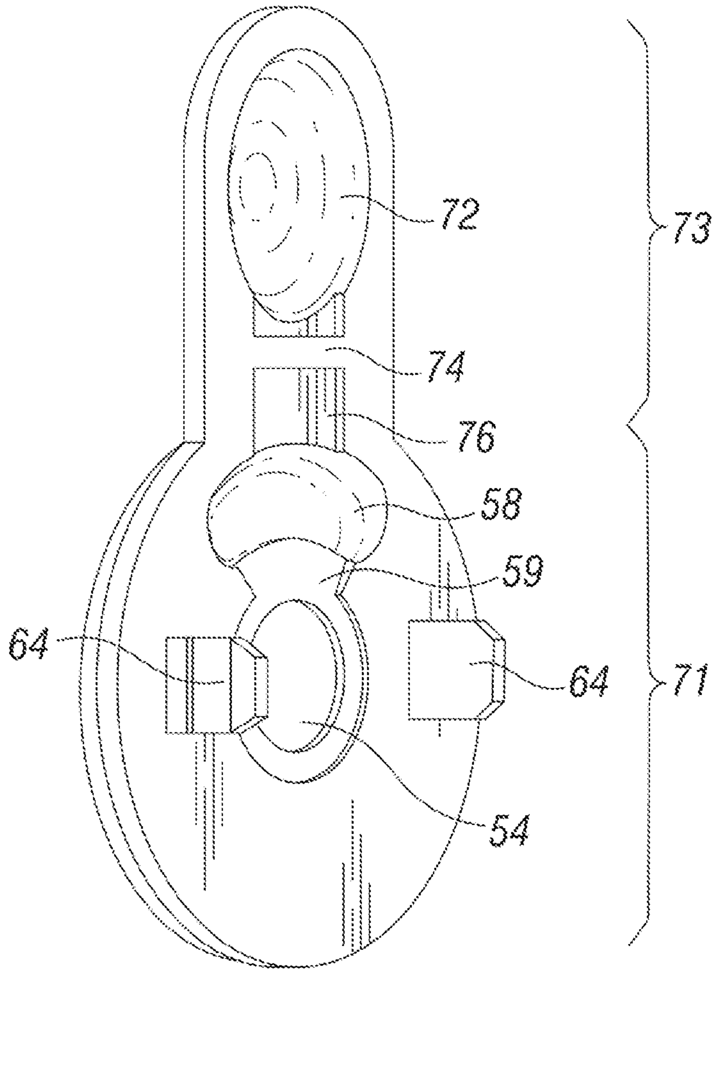
FIG. 4 is view of a disposable aerosolizing element without a backing member.

FIG. 4 illustrates another embodiment of a disposable aerosolizing element 70. Disposable aerosolizing element comprises a disk-shaped portion 71 that is received adjacent to nasal prong 14 and an extending portion 73 that extends away from the disk-shaped portion 71. The structure of disposable aerosolizing element 70 (FIG. 4) is similar to that of disposable aerosolizing element 50 (FIG. 3). Disposable aerosolizing element 70 has an opening 54, which can be covered by a mesh element (not shown) on one side and a backing element (not shown) on the other. A reservoir 58 can be used to deliver a treatment agent via one or more fluid-feed channels 59.

In addition, unlike disposable aerosolizing element 50 (FIG. 3), disposable aerosolizing element 70 (FIG. 4) comprises extending portion 73 which houses an external blister-sealed storage reservoir 72. Storage reservoir 72 can be used to hold the treatment reagent apart from reservoir 58 and mesh element 56 prior to use. For example, a backing element can be secured to the back of disposable aerosolizing element 70, including over storage reservoir 72 thereby containing a treatment agent in storage reservoir 72. The backing element can comprise, for example, a backing film which is heat-sealed onto the back (e.g., rear side) of disposable aerosolizing element 70. Pressure can be applied to storage reservoir 72 to transfer the treatment agent from storage reservoir 72 to dispensing reservoir 58 for aerosolization of the treatment agent. For example, storage reservoir 72 can be squeezed between a finger and thumb, thereby rupturing a barrier seal 74 positioned between storage reservoir 72 and dispensing reservoir 58, and allowing the treatment agent to flow through a transfer port 76 into dispensing reservoir 58.

Figure 5:
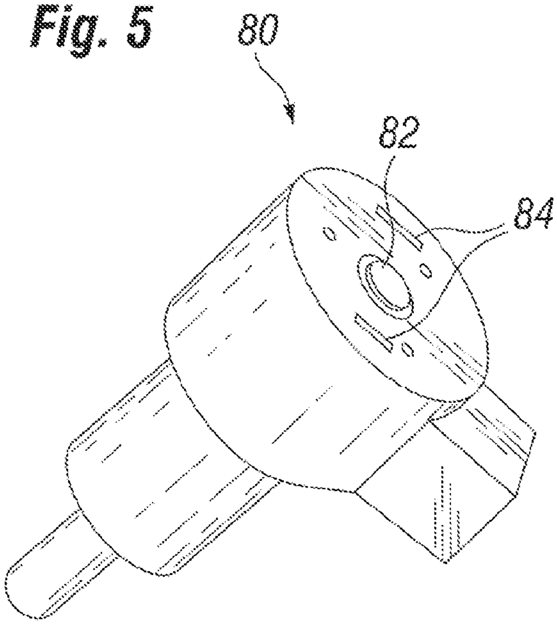
FIG. 5 is a view of a nebulizing device for use with a nasal delivery device.

FIG. 5 illustrates a nebulizing device 80 that can be used in connection with the disposable aerosolizing elements described herein. Nebulizing device 80 is configured to apply a moving force to the disposable aerosolizing elements. For example, in use the disposable aerosolizing elements can be positioned on or against nebulizing device 80 so that a motion transmitting member 82 of nebulizing device 80 applies an oscillating force to the disposable aerosolizing element causing the treatment agent to be expelled through the mesh element as aerosol droplets. Motion transmitting member 82 can be caused to move back and forth using any type of oscillator that can apply vibratory oscillations to the disposable aerosolizing element.

For example, as discussed in U.S. Patent Application No. 2009/0223513, which is incorporated by reference herein, the actuator can comprise a piezoelectric-driven actuation (also known as an ultrasonic horn) that includes first and second electrodes and a piezoelectric element disposed between the two electrodes. The motion transmitting member 82 can be coupled to the first electrode. An oscillating electric current can be applied to the two electrodes, thereby inducing vibratory motion of the piezoelectric element, which in turns induces vibratory motion of motion transmitting member 82. The motion transmitting member 82 transmits the vibratory motion to the disposable aerosolizing element for aerosolizing the treatment agent therein. In particular embodiments, an actuator can generate vibrations in the range of about 20 to 200 kHz. It should be understood that other types of actuators, such as a solenoid or a linear electric motor (e.g., a voice coil, such as used in a loudspeaker), also can be used to induce vibration and/or movement of motion transmitting member 82 in order to aerosolize the treatment agent.

Preferably, the motion transmitting member 82 is generally aligned with the mesh element 56. To facilitate this alignment, the disposable aerosolizing element is preferably secured to the nebulizing device 80. For example, tab members 64 can be inserted into receiving slots 84 (FIG. 5) to secure the disposable aerosolizing element to the nebulizing device 80.

Figure 6:
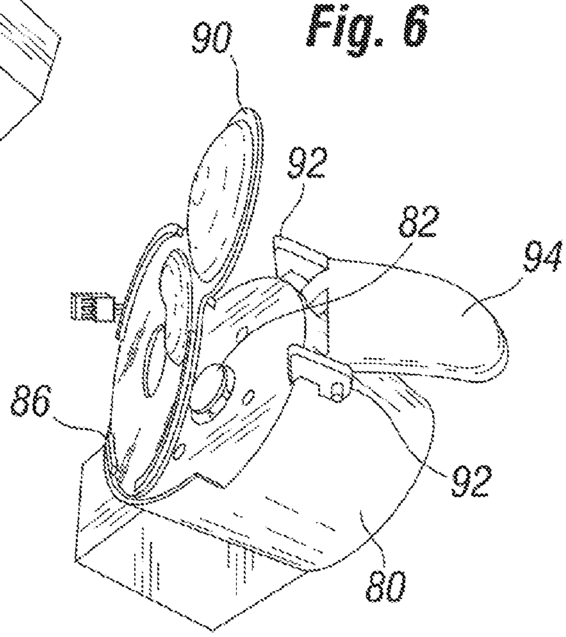
FIG. 6 is a view of a disposable aerosolizing element partially positioned on a nebulizing device.
Figure 7:
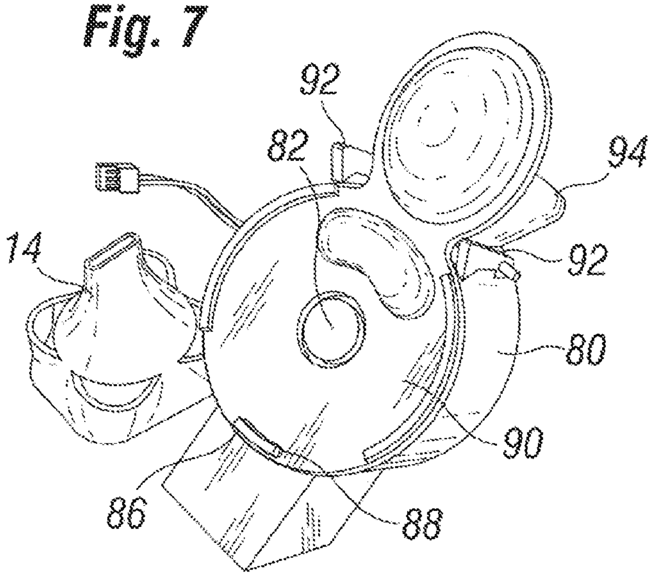
FIG. 7 is a view of a disposable aerosolizing element secured to a nebulizing device.

Alternatively, or in addition to tab members extending from the disposable aerosolizing element, various securing mechanisms can be provided to hold a disposable aerosolizing element in position adjacent a motion transmitting member of a nebulizing device. As shown in FIGS. 6 and 7, for example, nebulizing device 80 can include one or more tab members 86 that extend from a surface of nebulizing device 80 to be received in a corresponding opening or slot 88 in a disposable aerosolizing element 90. To better illustrate the positional relationship between disposable aerosolizing element 90 and nebulizing device 80, disposable aerosolizing element 90 is shown in FIG. 7 without a mesh element or backing member.

One or more retaining members 92 can extend from nebulizing device 80 and extend at least partially around a portion of disposable aerosolizing element 90 to further secure disposable aerosolizing element 90 to nebulizing device 80. To facilitate the release of disposable aerosolizing element 90 from nebulizing device 80 a pivoting lever (thumb-activated release) 94 can be provided. By applying a downward force to pivoting lever 94, retaining members 92 are pivoted or moved upward and away from disposable aerosolizing element 90, thereby allowing disposable aerosolizing element 90 to be removed for disposal.

Figure 8:
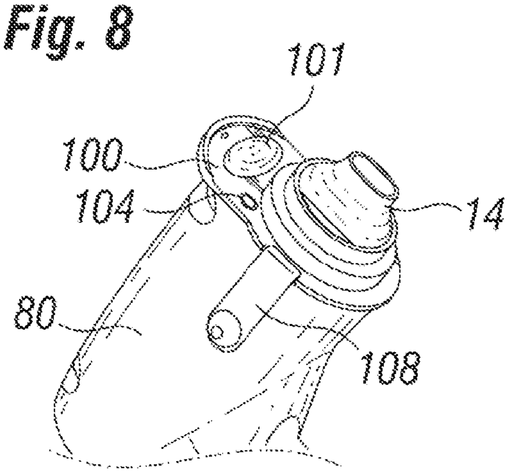
FIG. 8 is a partial view of a nasal delivery device with a disposable aerosolizing element secured adjacent to a nebulizing device.
Figure 9:
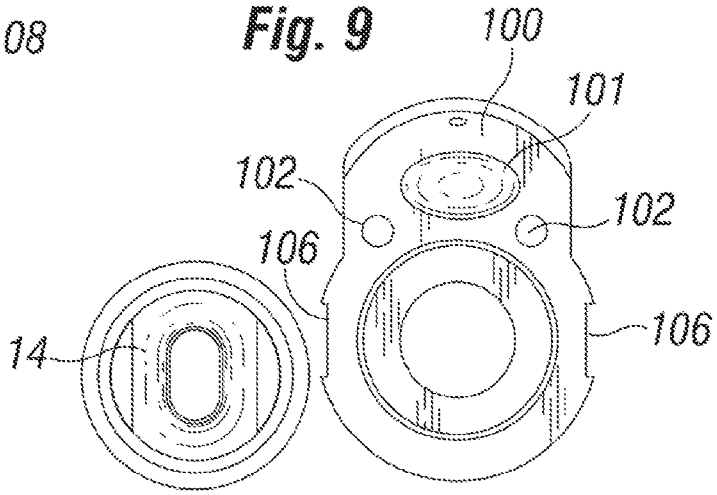
FIG. 9 is a view of a nasal prong and a disposable aerosolizing device.

FIGS. 8 and 9 illustrate another embodiment of a disposable aerosolizing element. Disposable aerosolizing element 100 has a plurality of openings 102 for receiving securing pin members 104 that extend from nebulizing device 80. In addition, one or more notches 106 are formed in disposable aerosolizing element 100 to facilitate the attachment of disposable aerosolizing element 100 to nebulizing device 80. In particular, two spring clips (e.g., stainless steel spring clips) 108 can extend from nebulizing device 80 and extend into the respective notches 106 of disposable aerosolizing element 100 to secure disposable aerosolizing element 100 to nebulizing device 80. Disposable aerosolizing element 100 also comprises a storage reservoir 101 for storing treatment reagent prior to aerosolization and delivery of the treatment agent to the subject.

Figure 10:
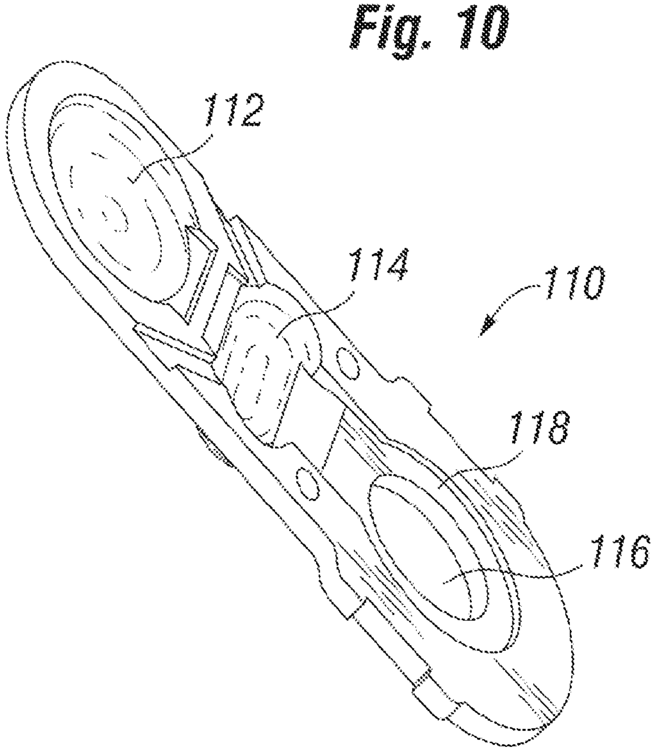
FIG. 10 is a view a disposable aerosolizing element without a backing member.

FIG. 10 illustrates another embodiment of a disposable aerosolizing element with an increased cavity depth in the area surrounding an opening and mesh element. Disposable aerosolizing element 110 comprises a storage reservoir 112, a dispensing reservoir 114, and an opening 116. Opening 116 is configured to be covered with a mesh element (not shown) as discussed above. In addition, as discussed above, a backing member (not shown) can be provided over the back of disposable aerosolizing element 110 to contain the treatment agent. To improve fluid flow in the area surrounding opening 116 (i.e., the area surrounding the mesh element), a cavity 118 is preferably provided between the front and back surfaces of the disposable aerosolizing element 110, with cavity 118 at least partially surrounding opening 116.

Figure 11:
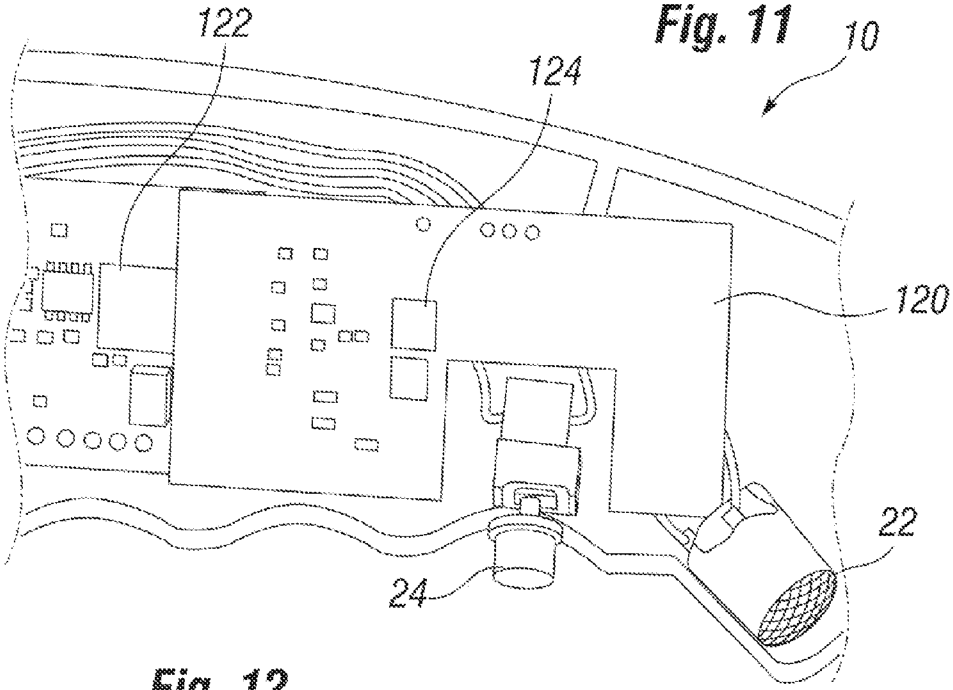
FIG. 11 is a partial view of an internal structure of a nasal delivery device with a remote activation member.

Returning to the structure of nasal delivery device 10, FIG. 11 is a view of the internal components of a portion of device 10. As shown in FIG. 11, a circuit board 120 can be provided within device 10. Circuit board 120 can be coupled to activation member 22 and can be used to deliver an activation signal from activation member 22 to the nebulizing device (not shown). Upon receiving the activation signal from activation member 22, nebulizing device begins aerosolizing the treatment agent held in the disposable aerosolizing element by causing the motion transmitting member to apply an oscillatory force to the disposable aerosolizing element.

A dose timing control switch 122 can be provided to control the length of time that the nebulizing device delivers the treatment agent (i.e., the length of time the treatment agent is caused to be aerosolized) after activation member 22 is activated. Thus, the dose timing switch 122 can be configured to deliver a short dose or long dose when the target exhalation action is determined by activation member 22 (e.g., sound-detecting microphone). A mode switch 124 (preferably accessible or changeable via an external switch or button) can be provided to allow the device to be switched between a remote activation mode which utilizes the remote activation member and a manual mode whereby the dose delivery is triggered upon activation of trigger 24 (e.g., independent of the remote activation member).

As noted above, the microphone or other sound-detecting device can be configured to detect flow noise that is generated by the subject's breath blowing over the microphone or a sound generating member or obstacle adjacent the microphone, such as a screen. When the device is in the remote activation mode, upon reaching a predetermined threshold sound level, the activation device causes the nebulizing device to be activated, which aerosolizes the treatment agent and delivers it through the nasal prong to the subject.

Alternatively, other noise generating mechanisms can be used in conjunction with the microphone. For example, a whistle or kazoo type device can be positioned in an area of exhalation breath flow. The whistle or kazoo can be constructed to generate a sound or tone when an exhalation flow is directed towards the noise generating mechanism and falls with a desired flow range. The sound or tone generated by the whistle or kazoo can be detected by the microphone and, if the sound level falls within a predetermined range, the actuation member can trigger the deployment of the treatment agent.

Figure 12:
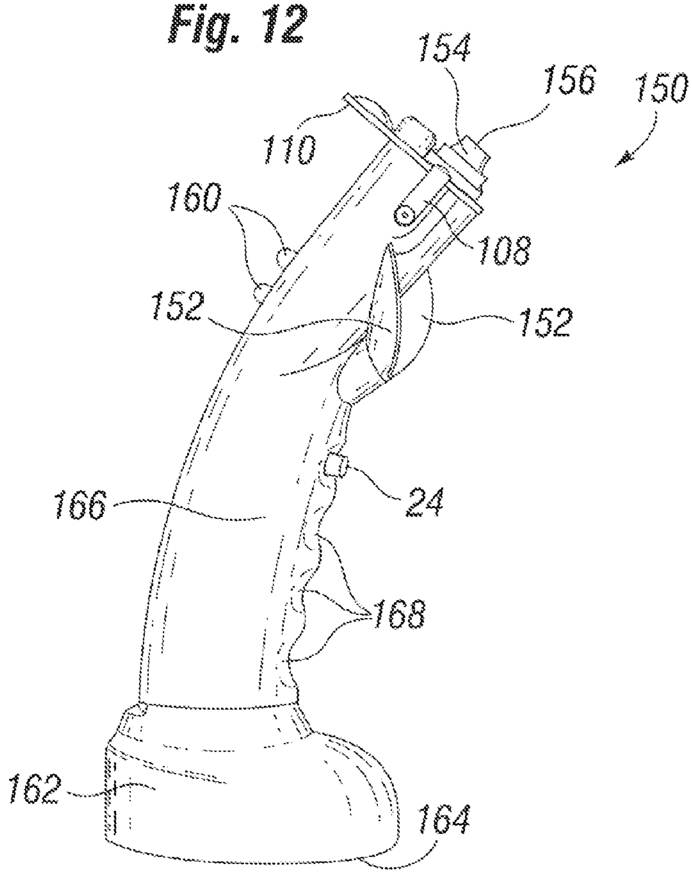
FIG. 12 is a side view of a nasal delivery device with a remote activation member.

FIG. 12 illustrates another embodiment of a remote activated nasal delivery device. Delivery device 150 is similar to device 10, with the following differences. Breath deflector 152 is positioned to at least partially deflect oral exhalation towards the activation member (e.g., microphone). Since the device is preferably constructed so that it can be used in either naris, a central location of the activation member can cause the microphone to be misaligned with the flow of air from the subject's mouth during an oral exhalation. However, by providing breath deflector 152, the exhalation breath of a subject can be directed across or at activation member 158 regardless of the facial geometry of the subject or the lateral position of the device relative to the subject's face.

Breath deflector 152 can comprise a one or more wall members that at least partially surround the activation member to increase the sensitivity of the activation member to noise generated from air flow associated with an exhalation breath. For example, as shown in FIG. 12 and FIG. 22B, activation member 158 can be positioned between one or more walls of a breath deflector 152 so that breath deflector 152 at least partially surrounds activation member 158.

The tip (opening 156) of nasal prong 154 and activation member 158 are preferably spaced at least about two inches apart, and more preferably at least about three inches apart, and even more preferably at least about four inches apart. By positioning the activation member two inches, three inches, four inches, or more from opening 156, the likelihood that a subject's mouth will directly contact the activation member during use of the device can be greatly reduced.

LEDs or other indicators 160 can be provided on the device to indicate whether the device is ready and whether the nebulizer (aerosol delivery device) is on. Device 150 preferably has a base member 162 that has a substantially flat bottom surface 164, so that the device can rest on a flat surface (such as a table) for dose delivery to provide for a more stable delivery of the treatment agent. Also, for the comfort and convenience of the dose administrator, device 150 preferably has a handle portion 166 with contoured portions 168 for receiving the fingers of the dose administrator (e.g., a pistol-style grip).

In operation, when the device is in remote activation mode, pushing trigger 24 causes the activation member to be turned on to a ready state for detecting an exhalation or other breath condition. If desired, an LED can light up to indicate the "ready" state of the activation member and nebulizing device. Then, when an oral exhalation is detected by the activation member, the nebulizing device is activated and a motion transmitting member causes the aerosolization of the treatment agent aerosol and delivery of the aerosolized treatment agent through the nasal prong and into the subject's nasal passages. If desired, a second LED can light up to indicate the "delivery" state of the device. The delivery state is active (LED is on) when the nebulizing device is in an aerosolizing mode and inactive (LED not on) when the nebulizing device is in a non-aerosolizing mode.

As discussed above, the activation member can be a microphone or other similar device. Alternatively, other methods can be used to detect an exhalation breath using a remote activation member. For example, air flow can be detected using a pinwheel, deflecting foil, or other similar flow sensor that is positioned on the device away from the subject's oral cavity, but close enough to the oral cavity to detect an exhalation Like the microphone activation members discussed above, such an air flow sensor is preferably not in direct contact with the subject during use to prevent or reduce the likelihood of cross-contamination occurring between different subjects.

In other embodiments, the activation member can comprise a bone conduction microphone that is configured to be positioned away from nasal and oral contamination. For example, the bone conduction microphone can be configured to be received in the ear canal of a patient. If desired, the bone conduction microphone can be used in with a disposable earpiece cover to help avoid contamination between uses of the microphone with different patients. Because of the sensitivity and functioning of bone conduction microphones, they can be capable of identifying noise generation and/or vibrations within the mouth and nasal airways (e.g., by breathing or speaking), without regard of the noise levels of the environment. An example of a bone conduction microphone that is currently available and suitable for modification for use as an activation member as described herein is the ear-vibration microphones available through MFJ™. MFJ™ manufactures several devices that pick up vibration in an earbone when the user speaks or takes other actions (e.g., breather) that cause vibration in the user's earbone. In particular embodiments, the MFJ™ device includes a vibration pick-up microphone element that is a piezoelectric accelerometer microphone with an impedance of about 4.7 kΩ. Other suitable bone conduction devices that could be modified for use as an activation member include Aliph Jawbones™ and Gennum™ nx6000 Bluetooth headsets, as well as those manufactured by NS-ELEX™, which use a microphone to pick up air vibrations within a user's ear. Because the ear canal is remote and out of the way of nasal and oral passages, the use of bone conduction devices as an activation member can reduce the likelihood that infection will be transmitted through nasal discharge and/or saliva.

In other embodiments, chest wall or diaphragm motion and/or noises can be used as a trigger for remote activation. The chest and diaphragm move (e.g., expand and contract) when an individual breaths in and out. Accordingly, simple motion sensors can be placed on a patient's clothing to detect a breathing state of the patient, which can then be used to trigger activation of an activation member. Movement of the chest wall or diaphragm can also be detected by using an optical sensor, such as those used by an optical computer "mouse." Such an optical sensor could detect the motion of the chest wall or diaphragm by optically comparing changes in the position of a person's clothing or a disposable target placed on the chest or diaphragm in response to the contraction of the chest or diaphragm during exhalation. Optical mapping and comparison devices can be entirely non-contact to further decrease the risk of contamination of the delivery device.

Alternatively, an abdominal or chest contact microphone can be positioned adjacent the chest or abdomen to detect sounds generated within the lungs during breathing. Such sounds can be used to trigger the remote activation of the devices.

In other embodiments, the activation member can comprise a humidity or temperature sensor. Since exhaled breath has a higher humidity and temperature than ambient air, a fast-response humidity or temperature sensor can be effective to determine when a subject undergoes an exhalation.

In other embodiments, the activation member can comprise a chemical sensor. For example, since an increased amount of carbon dioxide is present in exhaled breath, a sensor that detects the presence, of or an increase in, carbon dioxide can determine when a patient exhales. Similarly, prior to vaccination, a subject can be provided with a substance (such as a lozenge or chewing gum) that emits a chemical tracer that can be detected in their exhalation by a chemical sensor.

Upon detection of an exhalation (e.g., by sound, chemical, or other means), a visual indication can be provided to the individual administering the dosage. For example, an LED can be illuminated indicating that an exhalation is occurring. Alternatively, or in addition, an audible signal can be provided when a sound-generating activation member is used (e.g., a kazoo or whistle).

In the embodiments provided above, the delivery of the aerosolized treatment agent to the nasal passages occurs solely through the air flow induced by the aerosol droplet ejection caused by the vibrating mesh element. However, if desired, additional air flow can be provided to facilitate the delivery of the treatment agent through the nasal passages and to help overcome any nasal exhalation by the subject. For example, FIGS. 13A and 13B illustrate a device that uses additional air flow to assist the delivery of the treatment agent through the nasal passages.

It should be understood that the delivery devices disclosed herein can be configured to be single-naris or dual-naris devices. Although the treatment agent will be delivered somewhat differently in a dual-naris device, unless otherwise stated or directly contradictory to the described structure or method, either approach is generally acceptable for each of the embodiments described herein.

Figure 13A:
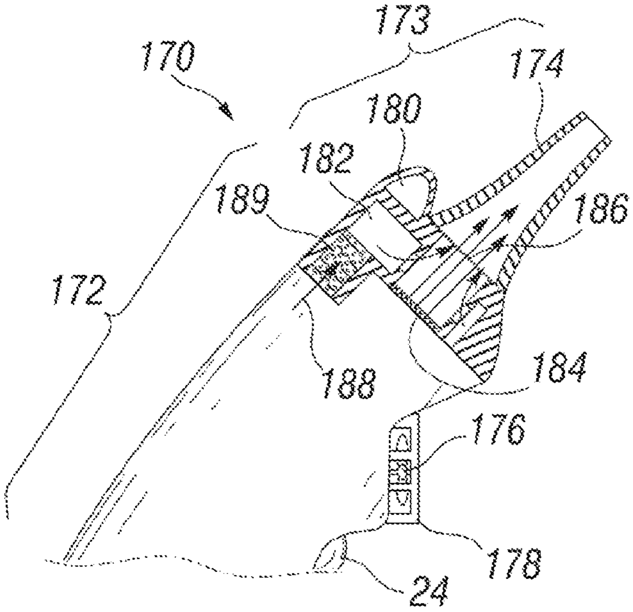
FIG. 13A is a partial cross-sectional view of a portion of a nasal delivery device that has a remote activation member.
Figure 13B:
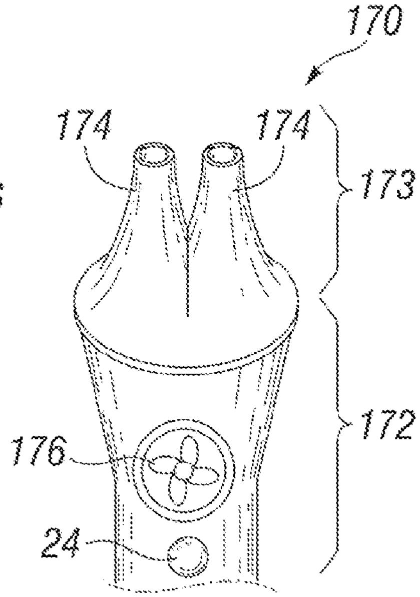
FIG. 13B is a front view of the nasal delivery device of FIG. 13A.

FIGS. 13A and 13B illustrate a dual-naris delivery device 170. In a dual-naris delivery device, the soft palate is preferably open during the administration of the treatment agent. Since aerosolized treatment agent is simultaneously delivered to both nares, the treatment agent will travel through both sides of the nasal cavity where most of the agent is deposited and then exit through the mouth. By triggering the administration of the treatment agent on an exhalation breath, the exhalation flow can substantially restrict the treatment agent from descending into the trachea and reaching the lower airways.

Device 170 comprises a nebulizing device 172 and a nasal delivery portion 173. Nasal delivery portion 173 comprises two nasal prongs 174. As in the embodiments discussed above, an exhalation sensor (activation member 176) is provided to detect oral exhalation and trigger aerosol generation. As with the other embodiments, the oral exhalation is preferably a gentle oral exhalation and, if desired, the exhalation sensor can be configured to disregard flow rates above a predetermined rate.

In the illustrated embodiment, activation member 176 comprises a pinwheel member that is configured to rotate when exhaled breath of a sufficient flow rate reaches the activation member. A shroud 178 can at least partially cover activation member 176. In a manner that is similar to the activation members of other embodiments, activation member 176 can be configured to activate the nebulizing device when the pinwheel member reaches a target rotational speed that is indicated of a desired exhalation breath.

A disposable aerosolizing element can be received between nebulizing device 172 and nasal delivery portion 173. The disposable aerosolizing element, like the other disposable aerosolizing elements disclosed herein, can comprise a storage reservoir 180, a dispensing reservoir 182, a backing member 184, and a mesh element 186. When the treatment agent is ready to be delivered, a force can be applied to storage reservoir 180, causing a barrier to rupture and allow the dose (i.e., the fluid containing the treatment agent) to enter into dispensing reservoir 182. From dispensing reservoir 182, the treatment agent can flow into the space between backing member 184 and mesh element 186, where it is then aerosolized through mesh element 186 by an ultrasonic horn (or other equivalent mechanism) that transmits oscillatory motion to the backing member 184.

As shown in FIG. 13A, an external air source (not shown), such as a pump, can deliver air 188 through the nasal delivery portion 173 to increase the flow rate of the aerosolized treatment agent and facilitate the delivery of the treatment agent through the nasal passages. If desired, an air filter 189 can be positioned between the air flow source and the disposable aerosolizing element to filter air 188 before delivering the air into the chamber of nasal prong 174. Air filter 189 can also prevent backflow of aerosol or contaminants into the nebulizing device. A ring manifold can be provided around the nasal prong to distribute the air flow to the prong. The filter and ring manifold (flow passages) can be part of the disposable aerosolizing element so that those elements are also disposable. By providing additional airflow, sufficient pressure can be provided to overcome any exhalation flow of the subject, thereby ensuring delivery of the treatment agent to the nasal passages of the subject.

The embodiments disclosed above generally relate to the detection of an exhalation breath to time the delivery of a treatment agent to a subject's nasal passages during the exhalation. Alternatively, it can be desirable to detect a condition or state where the subject is holding their breath (i.e., neither exhaling nor inhaling). Such a breath-holding or zero flow condition can be detected by the absence of an exhalation or inhalation air flow. Upon detection of a zero flow condition, the device can administer aerosolized treatment agent to a single naris. The soft palate can remain open during the administration; however, closure of the soft palate or velum is acceptable if it occurs. Aerosolized treatment agent can be delivered into a first naris, travel through one side of the nasal cavity, crossover in the posterior region of the nasal cavity, travel through the other side of the nasal cavity, and exit the nasal cavity via the other naris. The dosage amount is preferably sufficient to cause a desired amount of agent to be deposited within the nasal cavity where it can be absorbed by the body. Again, as discussed above, since the subject is not inhaling aerosol will not be drawn into the trachea or the lower airways.

Various methods can be used to detect a zero flow condition. For example, the devices described above can include an activation member that detects both the flow and non-flow of air. Thus, instead of activating upon the detection of an exhalation the devices can be activated during the detection of a zero flow condition. Alternatively, nasal delivery devices can be configured to provide a manual activation (e.g., using the trigger) and the activation members can be "deactivation members" which prevent manual activation when a particular flow condition is detected (e.g., any non-zero flow condition such as an exhalation or inhalation).

Figure 14A:
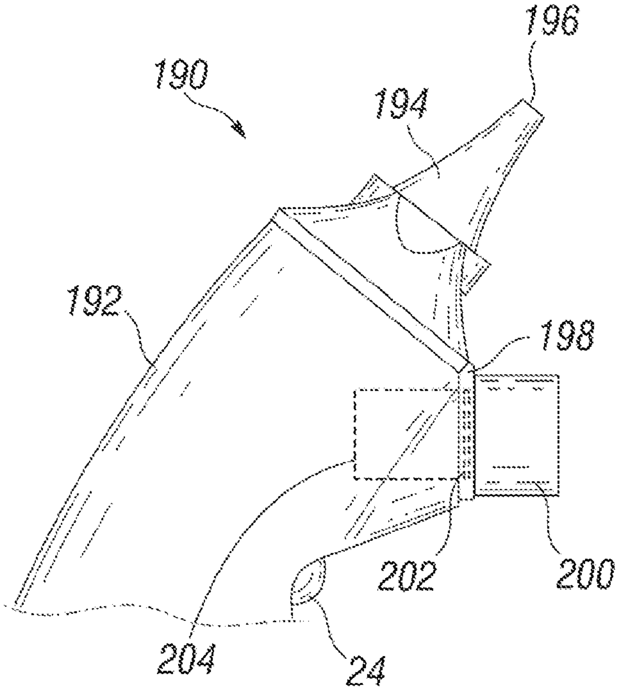
FIG. 14A is a side view of a nasal delivery device with an internal activation member.
Figure 14B:
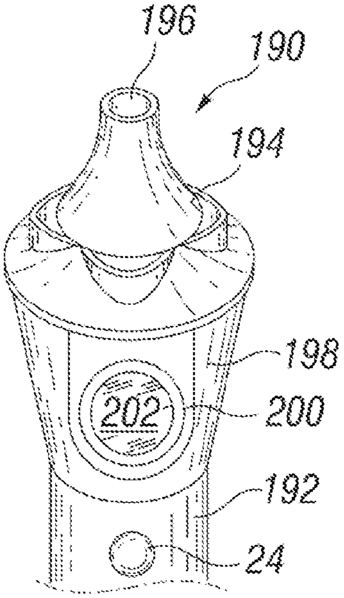
FIG. 14B is a front view of a nasal delivery device with an internal activation member.

FIGS. 14A and 14B illustrate another device capable of identifying a zero-flow condition and activating the nasal delivery of a treatment agent in response to the zero-flow condition. Device 190 can comprise a nebulizing device 192 and a vented nasal prong 194 with an opening 196. A disposable aerosolizing element (not shown) can be positioned between nebulizing device 192 and nasal prong 194, as described in other embodiments herein.

The disposable aerosolizing element can comprise an extending portion 198 that extends downward and that can be received in a subject's mouth. Extending portion 198 can comprise a port with a tube 200 attached to one end and a diaphragm 202 (such as a thin plastic diaphragm) attached to the other end. Tube 200 is preferably flexible to allow it to more easily fit the anatomy of various subjects. In operation, the subject can place tube 200 into their mouth, effectively sealing tube 200 with their lips. The subject then gently pressurizes tube 200 by holding his or her breath. Diaphragm 202 deflects under the pressure in tube 200 and the deflection of the diaphragm can be detected by an activation member (sensor) 204. Activation member 204 can comprise a proximity sensor which is capable of detecting slight deflections of diaphragm 202. The proximity sensor can be positioned within the handle of the nebulizing device and can comprise, for example, a laser or other sensor capable of detecting small motions.

Since the mouthpiece (flexible tubing) and diaphragm can be part of the disposable aerosolizing element, the portions of the device that are in contact with the oral cavity of the subject can be disposable.

Figure 15:
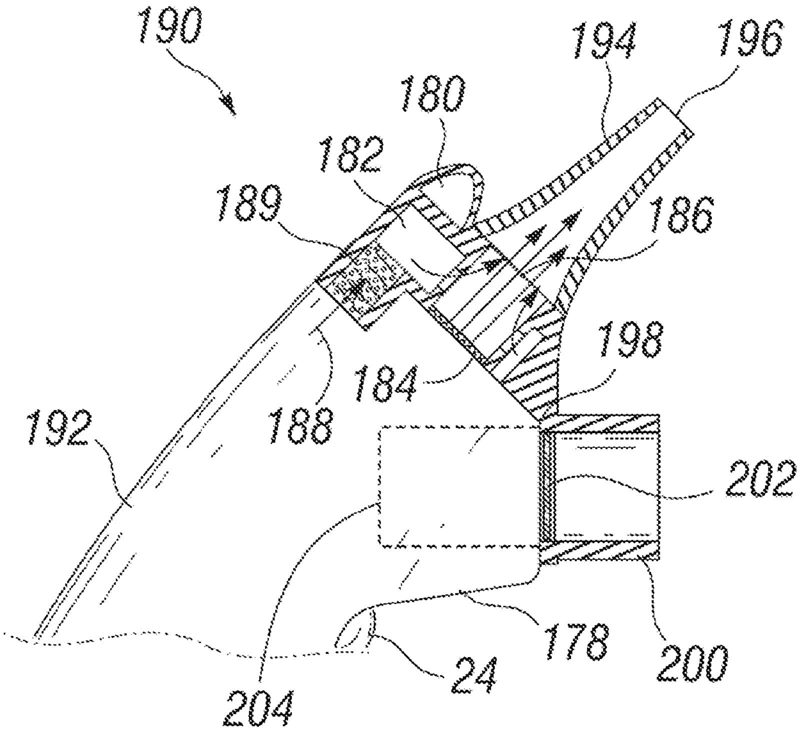
FIG. 15 is a partial cross-sectional view of a portion of a nasal delivery device that has an internal activation member.

As shown in FIG. 13A and FIG. 15, additional air flow can be generated in the various embodiments by adding an air flow source. FIG. 15 illustrates an embodiment of the zero flow device discussed above (FIGS. 14A and 14B) that also comprises a source for providing addition air 188 to increase air flow through the nasal prong 194. Air 188 can be pumped into the nasal prong as shown in FIG. 15.

As noted above, the various disclosed systems described herein allow for the administration of various types of agents, such as vaccines and other pharmaceutical substances. Use of the disclosed systems for agent delivery, such as for vaccination purposes, provide many benefits. For example, the present systems can replace the use of needles and syringes, and reduce the costs of agent delivery. Additionally, the present systems allows for treatment of patients by less-trained staff, another cost saving benefit, and also helps prevent the spread of blood borne diseases by reused needles.

Certain embodiments of the present system utilize an external activation member to trigger the delivery of the treatment agent. Because the activation member is external and no part of the activation member is received in an orifice of the patient (such as the oral cavity), the likelihood of cross-contamination of the activation member between patients is greatly reduced.

Moreover, when used with a disposable aerosolizing element that aerosolizes a treatment agent for delivery to a patient when acted upon by the actuator as described herein, the aerosolizing element prevents the agent from contacting the actuator and other non-disposable components of the system so that little or no cleaning or maintenance is required. Therefore, the systems described herein can be well suited for use by less-trained personnel in high-work-load applications, such as mass vaccination campaigns.

In other embodiments, devices and methods are provided to improve alignment of the nasal delivery device with a subject's specific anatomy to increase delivery and deposition of the aerosolized treatment agent in the target tissues.

It is desirable to align the intranasal aerosol device accurately to provide the optimal delivery of a treatment agent to a subject. In particular, many vaccines, such as live attenuated influenza vaccine, and other biological agents are desirably delivered to tissues that are deep inside the nose where immunologically active sites are located. Reaching these tissues by intranasal delivery requires that the aerosolized treatment agents pass through the nasal valve. The nasal valve is a narrow nasal airway that marks the boundary between the anterior part of the nose and the deeper regions of interest. Aerosolized treatment agents that fail to pass through the nasal valve can end up coating the anterior portion of the nose or otherwise dripping out of the naris. Since the targeted tissues are often deep within the nose and not within the anterior portion of the nose, aerosolized treatment agent that does not reach these regions can be medically ineffective.

Because intranasal anatomy can vary greatly from patient to patient (and even within the individual nares of a single subject), alignment of nasal delivery devices using exterior features only does not ensure that the aerosolized treatment agent will penetrate the nasal valve and reach the targeted tissues. The following embodiments provide real-time feedback of the alignment of a nasal delivery device with the nasal valve of each specific subject. As discussed in more detail below, these embodiments promote more effective delivery of aerosolized treatment agents by facilitating proper alignment of the nasal delivery device before the aerosolized treatment agent is delivered to the subject.

The following embodiments can be used with a wide range of aerosol delivery devices, including those with remote activation and/or zero flow activation members as described above. It should be understood that the alignment devices described herein can be used with vibrating mesh nebulizing devices as well as with other devices that are capable of ejecting an aerosol or spray plume to administer a treatment agent.

Figure 16:
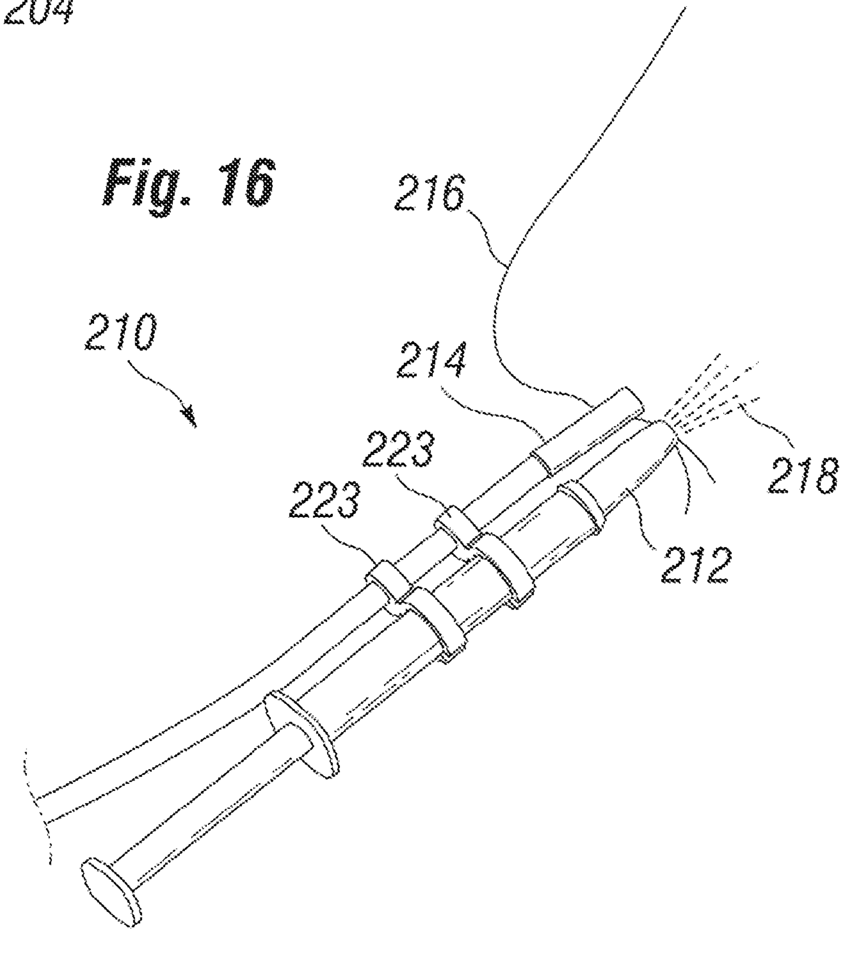
FIG. 16 is a perspective view of a nasal delivery device comprising an alignment device.

FIG. 16 illustrates an embodiment of a nasal delivery device that utilizes a reflectance measurement to facilitate proper alignment of the delivery device with the subject's naris. Nasal delivery device 210 can comprise a nasal prong 212 for delivering a treatment agent to a naris. Nasal delivery device 210 is shown in FIG. 16 as a syringe-style nasal sprayer; however, it should be understood that other nasal delivery devices could be provided (including, for example, the nasal delivery devices described in other embodiments herein).

A light source 214 (e.g., a light bulb, an LED, or a laser) can be configured to transmit light into the nasal airway of a subject along the same general axis as that which the delivered treatment agent 218 travels upon delivery into a subject's nose 216. The light source 214 can comprise one or more attachment members 223 that secure the light source to the nasal prong or nasal delivery device.

Figure 17A:
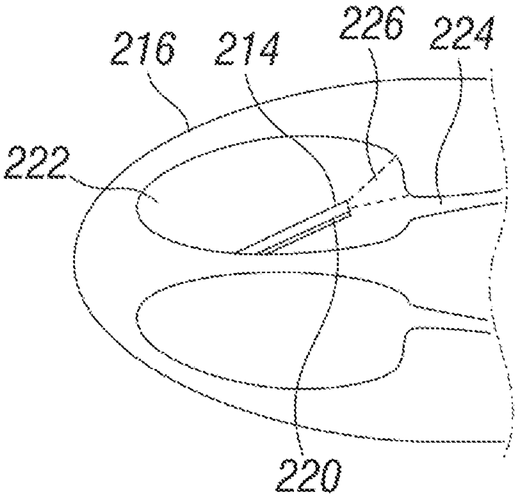
FIG. 17A is a schematic view of an alignment device positioned adjacent a naris and out of alignment with a nasal passageway.
Figure 17B:
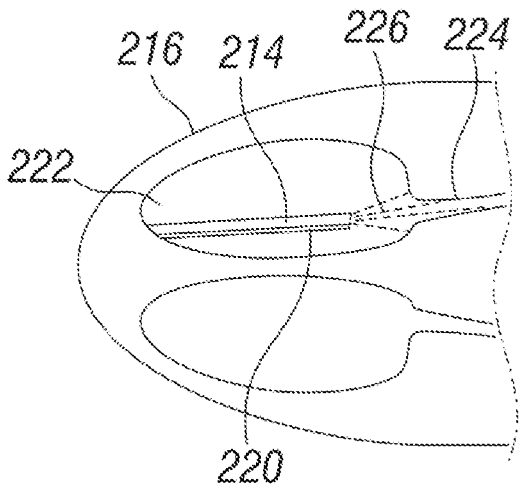
FIG. 17B is a schematic view of an alignment device positioned adjacent a naris and in alignment with a nasal passageway.

A light detector 220 (FIGS. 17A and 17B) positioned adjacent the light source 214 can measure or sense the amount of reflected light. Light source 214 and light detector 220 are desirably collinearly aligned as shown in FIGS. 17A and 17B. In a preferred embodiment, the optical alignment device (i.e., light source and light detector) are positioned external from the naris so that they are reuseable between subjects. Alternatively, a disposable protective cover can be received over the light source and detector to prevent cross-contamination between subjects.

FIGS. 17A and 17B illustrate a light source 214 and light detector 220 that cooperate to provide feedback about whether the nasal delivery device 210 is properly aligned for delivery of the treatment agent. FIG. 17A illustrates an example of a misaligned nasal delivery device and FIG. 17B illustrates an example of a properly aligned nasal delivery device. As shown in FIG. 17A, a light source 214 that is generally axially aligned with a nasal prong (not shown) can be positioned to direct light into a naris 222 of a nose 216. When light source 214 is directed toward an opaque surface, such as an inner surface of the naris that surrounds the nasal valve, the quantity of light reflected by the surface is relatively large and light detector 220 detects a strong signal. Thus, if the nasal prong is not properly aligned (FIG. 17A), a large amount of light 226 from light source 214 will reflect off of an inner surface of the naris and be received by light detector 220.

On the other hand, if the nasal prong is properly aligned (FIG. 17B), light 226 from light source 214 will enter into nasal airway 224 and light detector 220 will detect less light 226 reflected by a surface of the naris. Thus, alignment with the nasal airway (i.e., the nasal valve) corresponds to a minimal amount of light being reflected back to light detector 220.

Accordingly, by measuring the amount of light reflected to light detector 220, it can be determined when the device is not properly aligned (FIG. 17A) and the person administering the treatment agent can adjust the alignment of the nasal prong until the device is properly aligned for delivery (FIG. 17B).

Various light sources and detectors can be used to measure the reflectance and alignment of the nasal prong. For example, a small light source and detector can be mounted in close proximity to one another on an insertable device (e.g., a nasal prong) and aimed into the nasal airway. Alternatively, a pair of optical fibers connected to a diffuse illuminator (e.g., an LED) and a detector (e.g., a photodiode) can be provided to allow for greater flexibility in locating the optical components on a small insertable device. In another embodiment, the light source can comprise a coherent light source such as a laser.

In another embodiment, instead of measuring or detecting reflectance, a view into the naris of the subject can be provided to facilitate the alignment of the nasal delivery device. Such a view can comprise a direct view using an optical device or lens, or it can alternatively be an indirect view provided by lenses, mirrors, fiber optics, or video cameras and the like. In some embodiments, in addition to facilitating the alignment of an aerosol plume or delivery path, a visual approach as described herein can also allow the individual who is administering the treatment agent the ability to observe the aerosol plume or delivery path and verify the administration of the dose of the treatment agent.

Figure 18:
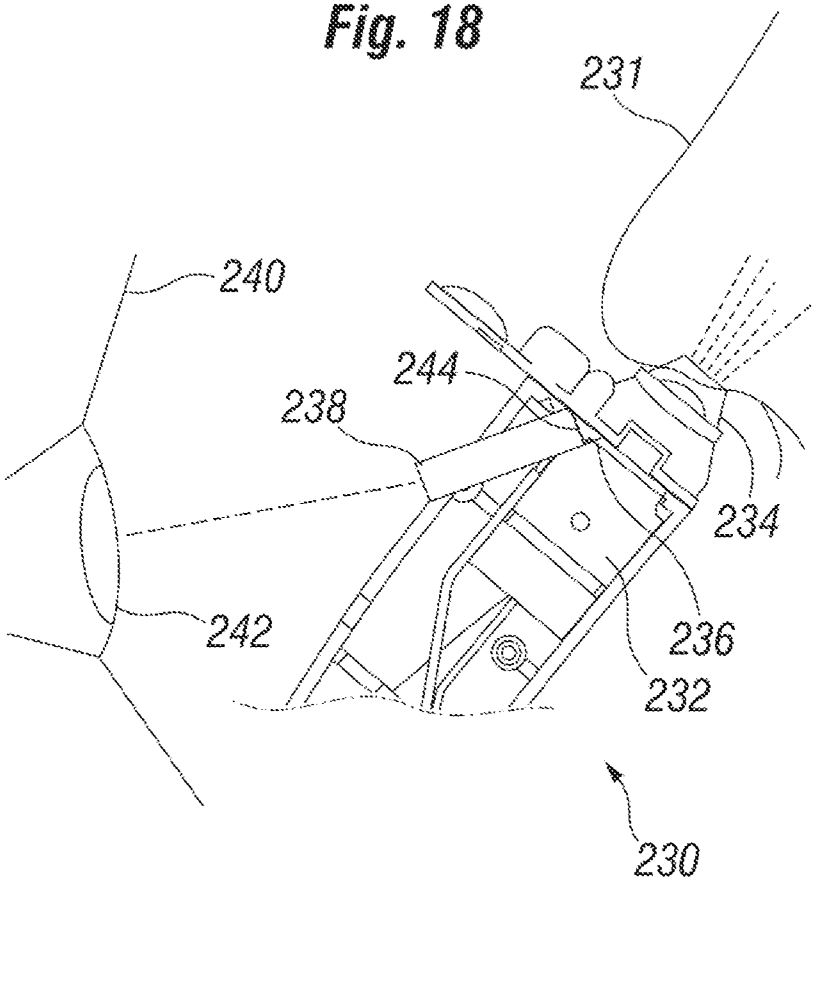
FIG. 18 is a partial cross-sectional view of a nasal delivery device comprising an alignment device.

FIG. 18 shows an embodiment of a nasal delivery device that includes an optical device that provides a direct view into a naris of a subject's nose 231. Nasal delivery device 230 comprises an aerosolizing device 232 with a nasal prong 234 configured to be received in a subject's naris. Device 230 can also comprise a light source 236 which at least partially illuminates the subject's naris. An optical device 238 is positioned adjacent aerosolizing device 232 so that optical device 238 is generally directed at the area at which the aerosol plume will be directed. Because optical device will be positioned at least somewhat off-axis with the aerosol delivery path, it may be desirable to angle optical device 238 slight to account for this off-axis alignment between optical device 238 and the delivery path of the aerosol. In addition, to provide the best view possible through optical device 238, optical device 238 preferably has a wide angle lens 244.

In operation, an individual 240 that is administering the aerosol treatment agent can look through optical device 238 with his or her eye 242 and determine whether nasal prong 234 is properly aligned with the subject's naris. If not, the individual can reposition nasal prong 234 until nasal prong 234 is properly positioned to deliver the aerosolized treatment agent into the subject's nasal airway. In its simplest form, the alignment device can comprise a tube with an eyepiece at one end and a lens at the other end (FIG. 18). In other embodiments, such as those discussed below, more complicated optical devices can be used to view (directly or indirectly such as by displaying an image) the inside of the subject's nostril.

Figure 19:
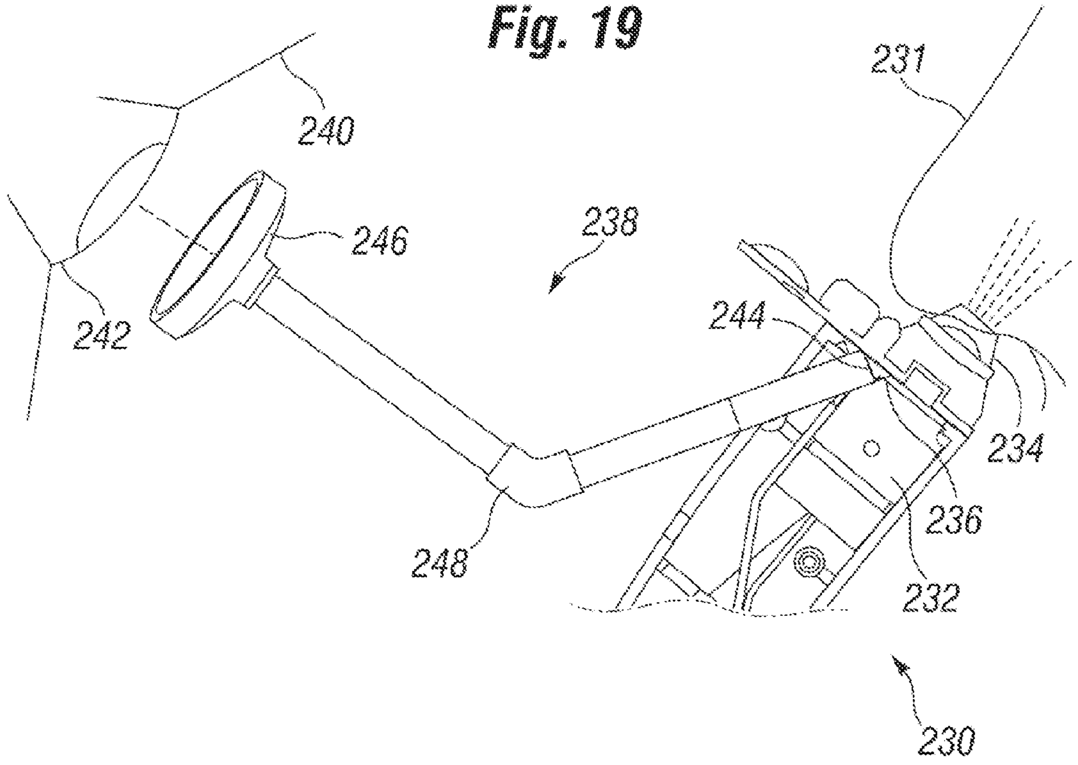
FIG. 19 is a partial cross-sectional view of a nasal delivery device comprising an alignment device.

FIG. 19 illustrates another embodiment of a nasal delivery device with an optical device. In FIG. 19, optical device 238 comprises an eyepiece 246 and a mirror 248 to provide an optical pathway that does not directly follow the line of sight of the individual administering the treatment agent.

Figure 20:
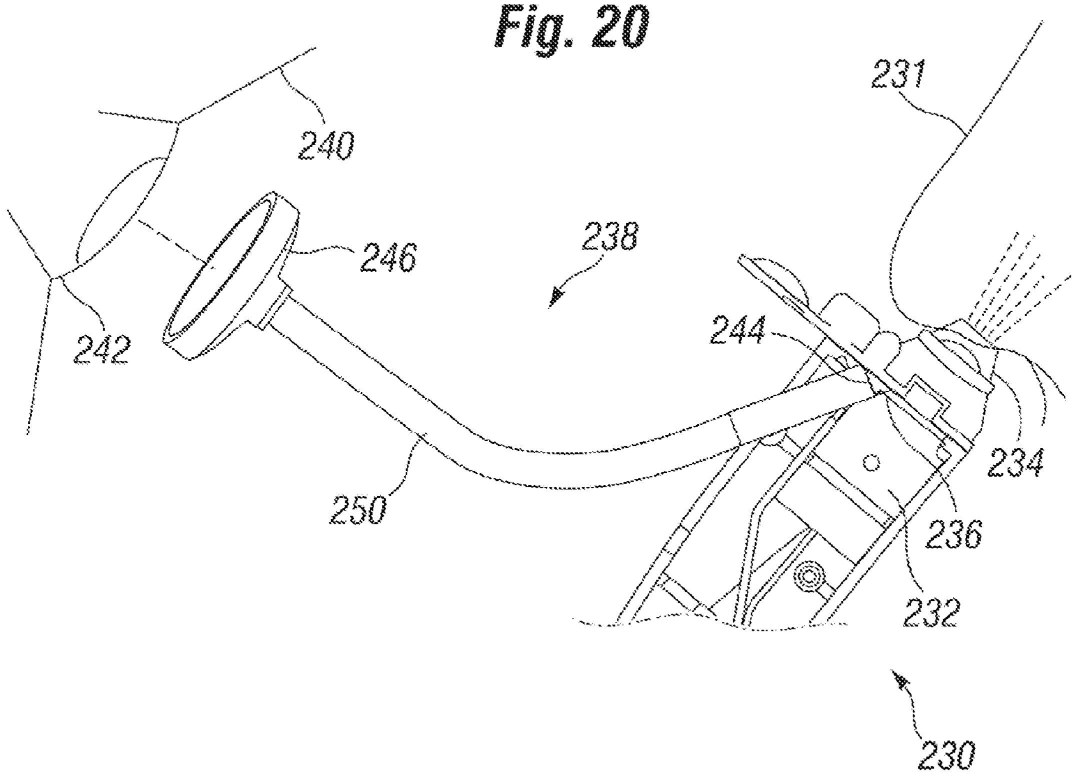
FIG. 20 is a partial cross-sectional view of a nasal delivery device comprising an alignment device.

FIG. 20 illustrates another embodiment of a nasal delivery device with an optical device. In FIG. 20, optical device 238 comprises an eyepiece 246 and again provides an optical pathway that does not directly follow the line of sight of the individual administering the treatment agent. However, instead of a mirror (FIG. 19), a fiber optic element 250 is provided to transmit the image to eyepiece 246. Fiber optic element 250 is preferably a coherent fiber bundle. Again, a light source 236 is preferably provided to illuminate an internal portion of the subject's naris so that the individual administering the treatment agent can see the anatomical features of the subject's naris. Using this approach, the alignment of the device can be readily achieved within 10 degrees from an optimal angle identified as the optimal aerosol plume delivery line, and more preferably within about 5 degrees from the optimal angle.

Figure 21:
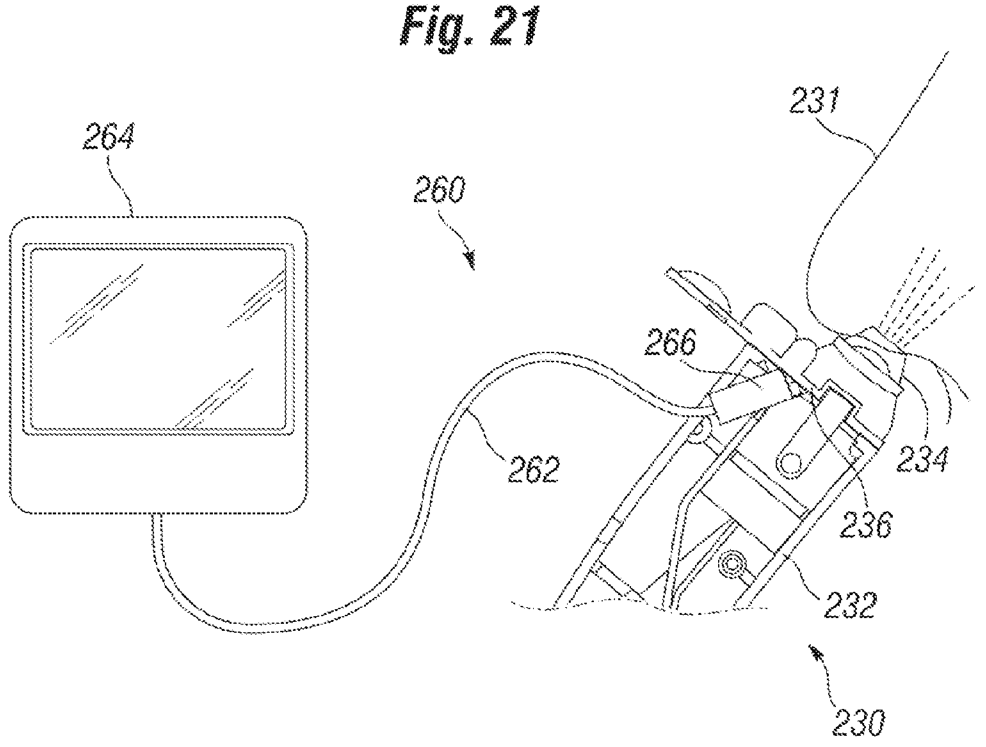
FIG. 21 is a partial cross-sectional view of a nasal delivery device comprising an alignment device that includes a display screen.

FIG. 21 illustrates another embodiment of a nasal delivery device with an optical device. The optical device 260 comprises a video camera 266 connected via a cable 262 to a video display 264. Images of the naris of the subject's nose 231 can be transmitted from video camera 266 to display 264 via cable 262. Alternatively, the images of the subject's naris can be wirelessly transmitted to the display so that the display and nasal delivery device are not tethered together. Light source 236 can be in the visible range or, alternatively, it can be in the infrared or other such range, and camera 266 can be configured to receive images based on the respective range of light provided by light source 236.

If desired, the video camera and display can be configured to improve the images and/or alignment of the nasal delivery device using a variety of digital or computer-generated features. For example, the viewing image can be enhanced (e.g., brightness or contrast adjustment, false color enhancement) to improve the clarity of the image. In addition, the area of the nasal valve can be identified by an automatic target recognition algorithm (e.g., an algorithm that seeks a dark region with the approximate shape of the nasal valve). The target can then be marked on the display by an illuminated rectangle or other symbol to help direct the individual administering the treatment agent to a proper alignment position. Moreover, in conjunction with target recognition and an electronically operated delivery device (e.g., a vibrating-mesh nebulizer as described herein), the delivery of the dosage can be automatically triggered to occur when the device is aligned with the target.

Figure 22A:
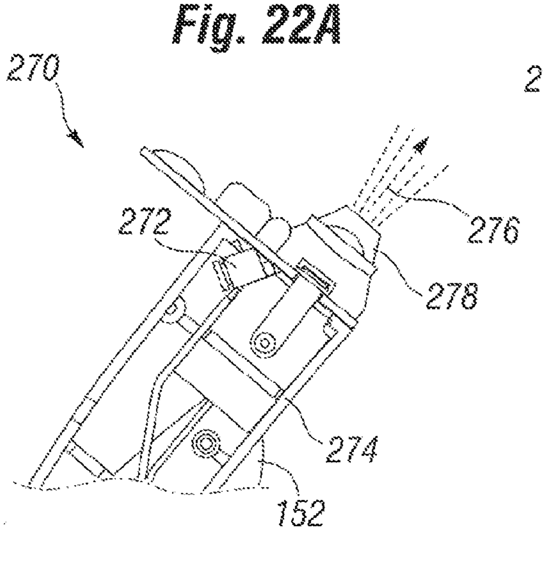
FIG. 22A is a partial cross-sectional side view of a nasal delivery device comprising an alignment device.
Figure 22B:
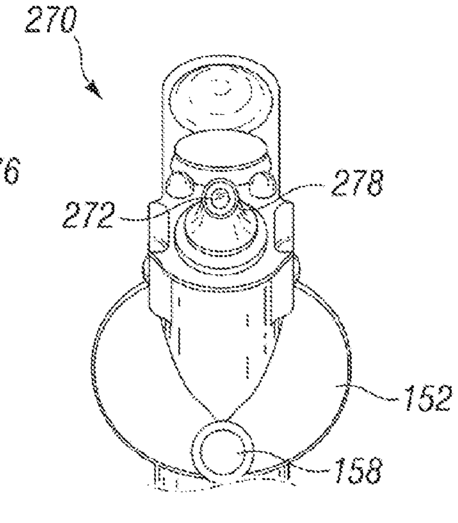
FIG. 22B is a partial cross-sectional side view of a nasal delivery device comprising an alignment device.

FIGS. 22A, 22B, 23A, and 23B illustrate a nasal delivery device 270 that has a miniature video camera 272 integrated with an intranasal nebulizer 274. Preferably, camera 272 has a wide field of view so that its viewing axis does not have to be identically aligned with the axis of the aerosol plume 276. The axis of the aerosol plume 276 (also called the delivery axis of the aerosolized treatment agent) is a central axis along which the aerosolized treatment agent is delivered. In some embodiments, a central, longitudinal axis of a nasal prong can at least partially define the delivery axis of the aerosolized treatment agent by acting to "direct" the aerosolized treatment agent along a particular delivery path. For example, as shown in FIG. 22A, the delivery axis of the aerosolized treatment agent (identified by arrow 276) is generally coaxial with a central, longitudinal axis of the nasal prong 278.

Figure 23A:
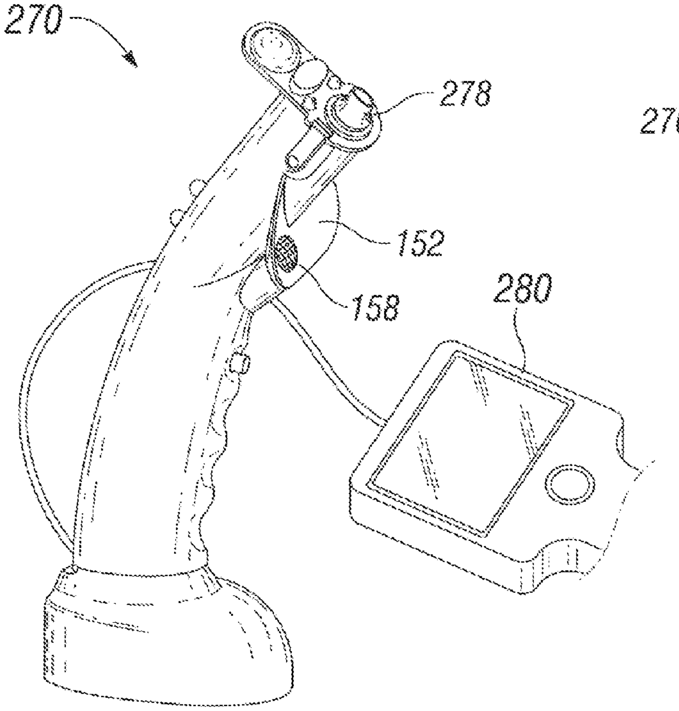
FIG. 23A is a perspective side view of a nasal delivery device comprising an alignment device that includes a display screen.
Figure 23B:
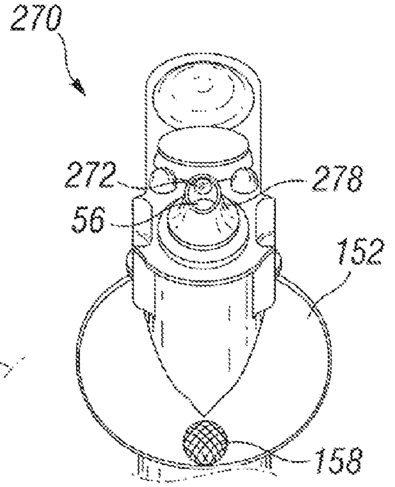
FIG. 23B is a front view of the nasal delivery device of FIG. 23A.

As shown in FIG. 22B, however, camera 272 preferably is substantially aligned with the axis of the aerosol plume. As shown in FIGS. 22B and 23B, by providing a line of sight of camera 272 that passes through nasal prong 278, the alignment of the axes of the line of sight of camera 272 and aerosol plume 276 can be generally acceptable. FIGS. 23A and 23B illustrate nasal delivery device 270 with a display screen 280 coupled to camera 272 to display the images received by camera 272.

Figure 24:
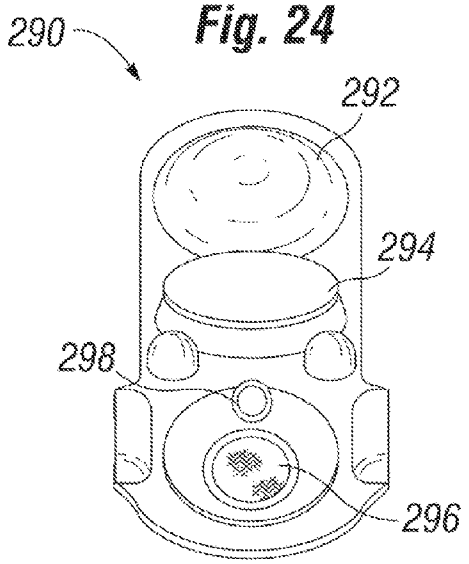
FIG. 24 illustrates a disposable aerosolizing element that includes a port for use with an optical device.

FIG. 24 illustrates a disposable aerosolizing element 290 that has been adapted to be received in a nasal delivery device that has a camera or other optical element. In particular, in addition to comprising a storage reservoir 292, a dispensing reservoir 294, and a mesh element 296 (as shown in FIG. 10), disposable aerosolizing element 290 also includes an optical port (opening) 298 to allow a camera or other optical element a clear view through the disposable aerosolizing element.

Figure 25A:
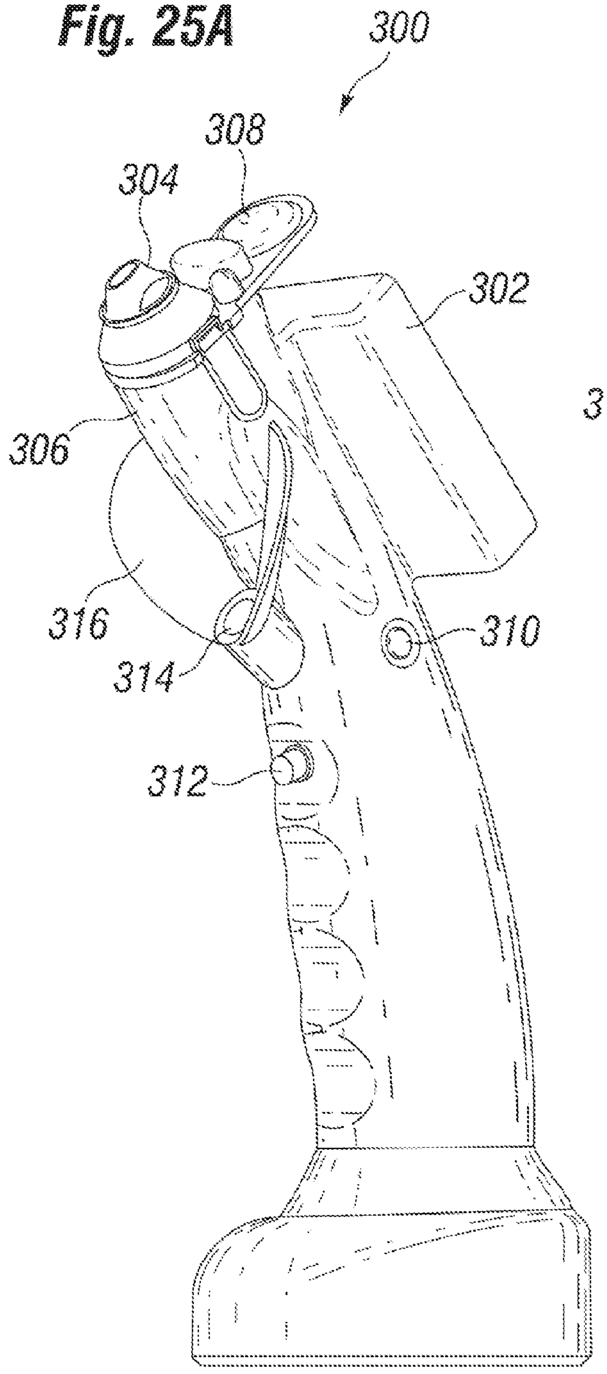
FIG. 25A is a front perspective view of a nasal delivery device comprising an alignment device that includes a display screen.
Figure 25B:
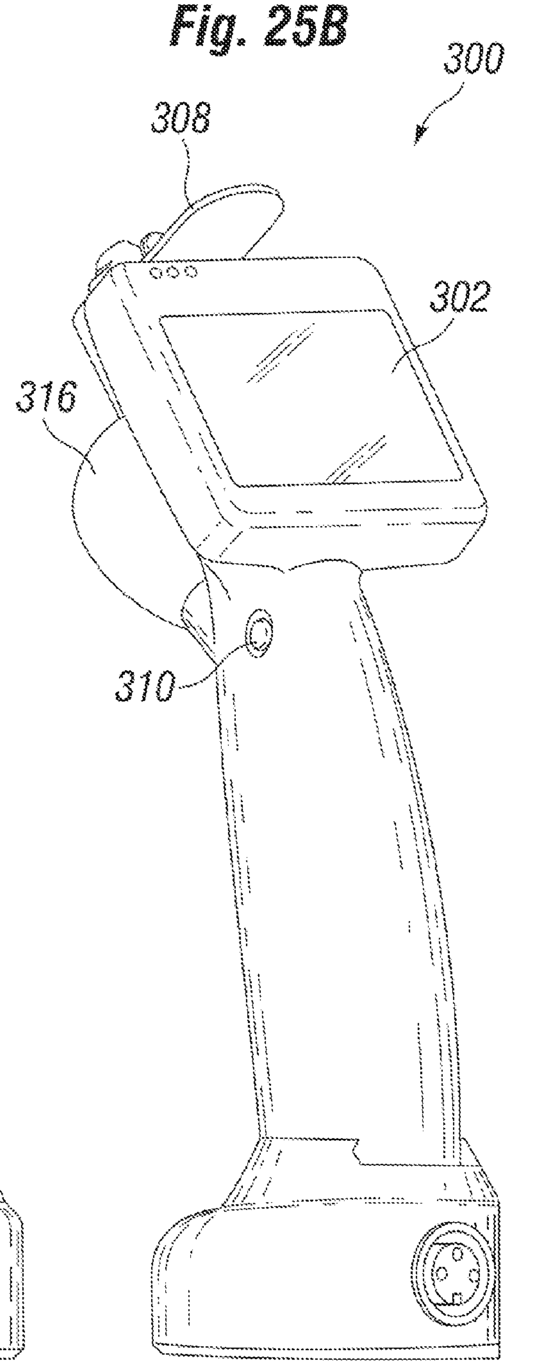
FIG. 25B is a rear perspective view of the nasal delivery device of FIG. 25A.
Figure 26:
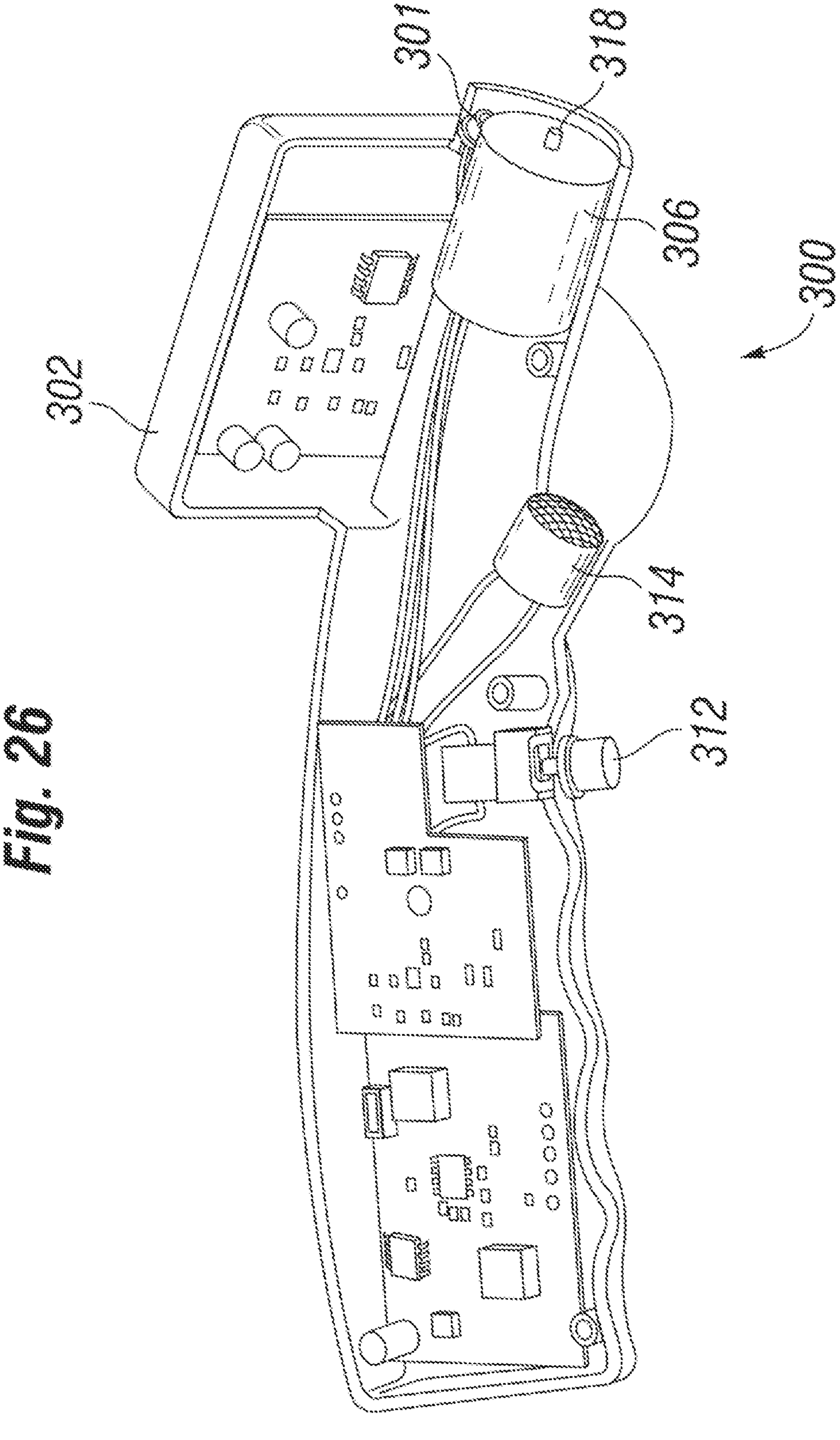
FIG. 26 illustrates a view of the internal structure of a nasal delivery device comprising an alignment device that includes a display screen.

FIGS. 25A, 25B, and 26 illustrate another nasal delivery device 300 that has a video camera 301 integrated with an intranasal nebulizer. However, instead of delivering images to an external, separate video display, a video display 302 is integrated into the device 300 itself. As shown and described in other embodiments, device 300 comprises a nasal prong 304 and a nebulizing device 306.

In operation, a disposable aerosolizing element 308 can be positioned between nasal prong 304 and nebulizing device 306. Disposable aerosolizing element 308 can be secured using one or more retaining members 309 which extend from the nebulizing device 306 and wrap at least partially around disposable aerosolizing element 308 to secure disposable aerosolizing element 308 to nebulizing device 306. A camera 301 can be provided with a view (e.g., via a direct line of sight) through disposable aerosolizing element 308 and nasal prong 304. The line of sight of camera 301 is preferably generally aligned with the delivery path of an aerosolized plume of treatment agent.

To activate the device, video display 302 can be powered on using switch 310, and a second trigger 312 can be activated to turn on an activation member 314 (such as a microphone). If the activation member 314 is a microphone or other similar structure, a breath deflector 316 can be provided to facilitate the detection of an exhaled breath by activation member 314. Upon detection of an exhalation, activation member 314 activates nebulizing device 306. Nebulizing device 306 can comprise a motion transmitting member 318 and upon activation of nebulizing device 306, motion transmitting member 318 begins to vibrate or otherwise move causing the treatment agent to be directed through the mesh element in an aerosol form. After passing through the mesh element, the aerosolized treatment agent is directed through nasal prong 304 and into the naris of the subject.

In some embodiments described herein, LEDs provide the desired illumination of the nares; however, it should be understood that other illumination elements can be used, including for example, light pipes, miniature filament bulbs, lasers, etc.

In some embodiments, the delivery device can be configured to automatically recognize a disposable aerosolizing element. For example, as shown in FIGS. 27A-29B, the disposable aerosolizing element can be provided with one or more means for identifying information about the disposable aerosolizing element. This information can include, for example, information about medication or other active agents contained therein, batch or source information relating to the disposable aerosolizing element's manufacture, information about the specific patient, or other helpful information about the disposable aerosolizing element, its contents, and/or the patient.

Such information can be keyed to the type of medication being dispensed by the disposable aerosolizing element and/or it can be keyed to patient-specific data (e.g., such as dosage). The delivery system can be configured to adjust its operation based on the information obtained from the disposable aerosolizing element about the medication or patient. In this manner, a single delivery device can administer different drugs in different ways (or the same drugs to different patients in different ways) to provide optimal delivery of a drug or other medication based on the recognition of a particular disposable aerosolizing element.

Settings that can vary based on medication-specific or patient-specific data include, for example, dose timing, voltage or frequency to the piezoelectric transducer, enabling/disabling of the delivery device and/or certain features of the device (e.g., breath activation or other activation features), settings for activation features (e.g., amount of breath required for breath actuation), and any other relevant operational features.

Figure 27A:
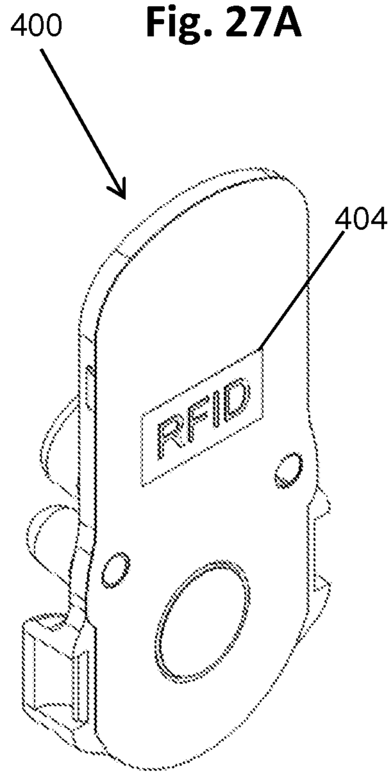
FIGS. 27A and 27B illustrate, respectively, a disposable aerosolizing element containing electromagnetic information and a portion of a delivery device configured to read the electromagnetic information contained on the disposable aerosolizing element.
Figure 27B:
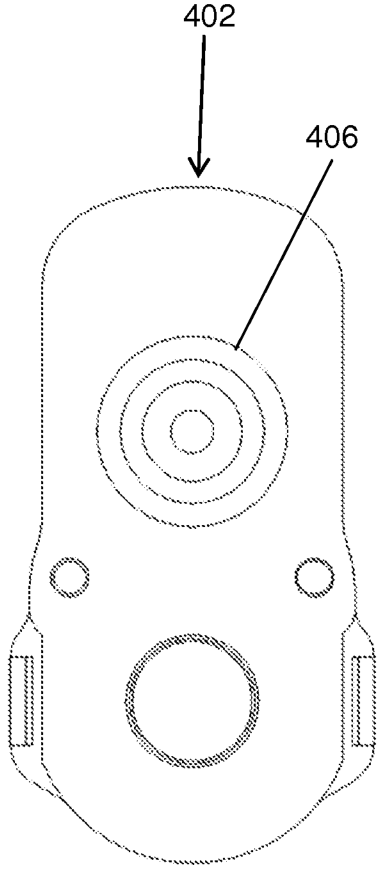

A delivery device can be configured to recognize the identity or type of a disposable aerosolizing element using, for example, electronic, optical, and/or mechanical means. For example, FIGS. 27A and 27B illustrate, respectively, a disposable aerosolizing element 400 and a portion of a delivery device 402. Disposable aerosolizing element 400 can comprise electromagnetic information 404 encoded or provided with the disposable aerosolizing element and this information can be read by a sensor 406 located on delivery device 402 when disposable aerosolizing element 400 is loaded into delivery device 402. The electromagnetic information 404 can comprise, for example, a radiofrequency identification tag (RFID) or a magnetic strip attached to or embedded in disposable aerosolizing element 400.

Figure 28A:
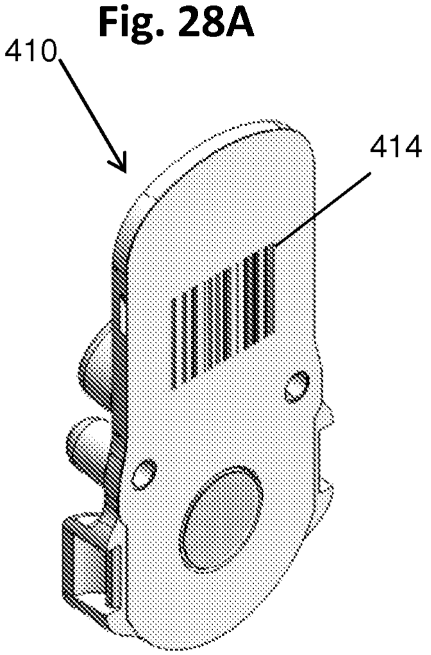
FIGS. 28A and 28B illustrate, respectively, a disposable aerosolizing element containing optical information and a portion of a delivery device configured to read the optical information contained on the disposable aerosolizing element.
Figure 28B:
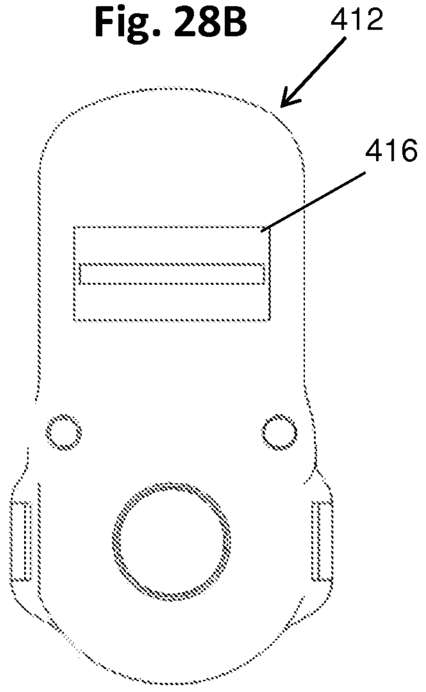

FIGS. 28A and 28B illustrate an optical recognition system. FIG. 28A illustrates a disposable aerosolizing element 410 that comprises an optical code 414 (e.g., a bar code) that can be ready by an optical sensor 416 provided on a delivery device 412.

FIGS. 29A and 29B illustrate a mechanical recognition system whereby mechanical features, such as the shape of a disposable aerosolizing element housing and/or the presence/absence of holes, tabs, or pins operate to help the delivery device identify and/or recognize the disposable aerosolizing element. FIG. 29A illustrates a disposable aerosolizing element 420 that can be received into a delivery device 422. Disposable aerosolizing element 420 comprises a unique shape (e.g., an ID key slot) that can be received into a matching delivery device slot 426 to provide the delivery device with information about the disposable aerosolizing element. In the mechanical recognition embodiments, the delivery system can be configured to read information about the disposable aerosolizing element by contact (e.g., by deflecting a structure on the delivery device) or by other indirect means (e.g., by blocking light transmission).

Various combinations of the recognition features described herein can be used. For example, the device can use mechanical recognition of the shape of the disposable aerosolizing element to detect the type of drug to be delivered but utilize a bar code or RFID tag applied by a pharmacist to control the specific dosing for the patient.

In some embodiments, the disposable aerosolizing element can also contain information or data related to one or more patients that can be recorded and maintained by the delivery system. This information can include, for example, the number of doses delivered, to which patient, and on what schedule. If desired, this information can be delivered (e.g., downloaded) from the device for review by a physician or other interested parties.

In addition to information about the type of drug, the disposable aerosolizing element can contain appropriate operational settings for the drug (permitting the delivery device to adjust itself automatically to the disposable aerosolizing element) and/or full settings for the delivery device (so that the device need not know the appropriate settings in advance). These settings can be programmed into the disposable aerosolizing element. If personalized information is provided, that information can include patient-specific data, such as dose time or breath actuation parameters in combination with drug type or device settings.

Disposable aerosolizing elements can be prefilled by the pharmaceutical manufacturer with the encoded information applied by the manufacturer, e.g., as indicated by the shape of the disposable aerosolizing element housing and/or one or more bar codes or RFID tags. Alternatively, disposable aerosolizing element can be filled by a compounding pharmacy with the encoded information applied by the pharmacy, e.g., by one or more bar codes or RFID tags. Disposable aerosolizing element can also be filled at the time of use by a medical professional or patient with the encoded information supplied with the drug, then attached to the disposable aerosolizing element. For example, the medication could be delivered in a vial with an accompanying peel-and-stick bar code.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A nasal delivery device for delivering a treatment agent in an aerosolized form to a subject, the device comprising:

a nasal prong comprising an opening at a top and bottom portion of the prong to allow for the passage of the aerosolized treatment agent through the nasal prong, at least a portion of the nasal prong being configured to be received into a nostril of the subject;

a nebulizing device having a motion transmitting member coupled to the nasal prong; and a remote activation member configured to detect an oral exhalation of the subject without coming into direct contact with the subject and generate an activation signal in response thereto, the remote activation member being positioned on the nasal delivery device at a location that is spaced apart from an oral cavity of the subject when the nasal prong is received into the nostril of the subject, wherein the nebulizing device has an aerosolizing mode and a non-aerosolizing mode, the remote activation member generating the activation signal to cause the nebulizing device to switch from the non-aerosolizing mode to the aerosolizing mode to deliver the aerosolized treatment agent through the nasal prong.

2. The nasal delivery device of claim 1, wherein the desired exhalation state is an oral exhalation and the activation member comprises a rotatable member that rotates upon exposure to the oral exhalation of the subject.

3. The nasal delivery device of claim 1, further comprising an air flow source, the air flow source being configured to direct air through the nasal prong to increase the air flow speed of the aerosolized treatment agent through the nasal prong.

4. The nasal delivery device of claim 1, further comprising:

a receiving area adjacent the motion transmitting member of the nebulizing device for receiving a disposable aerosolizing element, the disposable aerosolizing element comprising a housing that contains the treatment agent.

5. The nasal delivery device of claim 1, further comprising a dose timing switch that adjusts a length of time that the nebulizing device is in the aerosolizing mode after generation of the activation signal.

6. The nasal delivery device of claim 1, further comprising a deflector configured to deflect air flow generated by an oral exhalation of the subject towards the activation member.

7. The nasal delivery device of claim 6, wherein the deflector comprises one or more walls that at least partially surround the activation member.

8. The nasal delivery device of claim 1, further comprising a disposable aerosolizing element that comprises a housing that contains the treatment agent.

9. The nasal delivery device of claim 8, wherein the disposable aerosolizing element comprises a storage reservoir, a dispensing reservoir, and a temporary barrier restricting flow between the external and dispensing reservoirs, the temporary barrier being removable upon application of a physical force to the storage reservoir.

10. The nasal delivery device of claim 1, wherein the remote activation member is a microphone configured to detect a sound generated by air flow associated with the oral exhalation of the subject.

11. The nasal delivery device of claim 10, further comprising a sound generating member that generates a sound upon exposure to air flow associated with the oral exhalation.

12. The nasal delivery device of claim 11, wherein the sound generating member is a screen.

13. The nasal delivery device of claim 11, wherein the sound generating member is a whistle.

14. The nasal delivery device of claim 1, wherein the nebulizing device comprises a motion transmitting member configured to transmit an oscillatory force in the aerosolizing mode, the force being transmitted to a surface of a disposable aerosolizing device that is received in the nasal delivery device, and the disposable aerosolizing device contains a treatment agent.

15. The nasal delivery device of claim 14, wherein the disposable aerosolizing element comprises a storage reservoir, a dispensing reservoir, and a temporary barrier restricting flow between the external and dispensing reservoirs, the temporary barrier being removable upon application of a physical force to the storage reservoir.

16. The nasal delivery device of claim 15, wherein the disposable aerosolizing element comprises an optical port, wherein an optical device can be positioned into or adjacent the optical port to receive an unobstructed view through the disposable aerosolizing element.

17. The nasal delivery device of claim 1, further comprising a removable aerosolizing element the removable aerosolizing element comprising a body having an exterior surface and a chamber defined therein, a plurality of agent releasing orifices defined in the body and in communication with the chamber, and a movable element having an inner surface that defines a portion of the chamber, the movable element being capable of moving in response to an external force applied to the outer surface to expel agent in the chamber through the orifices.

18. The nasal delivery device of claim 17, further comprising at least one means for identifying information about the disposable aerosolizing element.

19. The nasal delivery device of claim 17, further comprising an optical sensor for identifying information about the disposable aerosolizing element.

20. The nasal delivery device of claim 17, further comprising an electromagnetic sensor for identifying information about the disposable aerosolizing element.

21. The nasal delivery device of claim 17, further comprising at least one sensor configured to provide identifying information about the disposable aerosolizing element based on a shape or structure of the disposable aerosolizing element.

22. The nasal delivery device of claim 1 for delivering an aerosolized treatment agent to the subject, wherein the nebulizing device is configured to aerosolize the treatment agent and generally deliver the aerosolized treatment agent along a delivery axis into the nostril of the patient, further comprising an alignment device for aligning the delivery axis of the aerosolized treatment agent with a nasal airway of the subject.

23. The nasal delivery device of claim 22, wherein the delivery axis of the aerosolized treatment agent is at least partly defined by the nasal prong through which the aerosolized treatment agent is delivered.

24. The nasal delivery device of claim 22, wherein the alignment device comprises a light source and a light detector that are generally coaxially aligned, the light detector detecting an amount of light reflected from a surface in the subject's nostril.

25. The nasal delivery device of claim 24, wherein upon detection of an amount of reflected light that is greater than a predetermined amount, the alignment device indicates that the delivery axis of the aerosolized treatment agent is not aligned with the nasal airway, and upon detection of an amount of reflected light that is less than a predetermined amount, the alignment device indicates that the delivery axis of the aerosolized treatment agent is aligned with the nasal airway.

26. The nasal delivery device of claim 22, wherein the alignment device comprises a light source that directs light into the nostril of the subject to facilitate alignment of the delivery axis of the aerosolized treatment agent with the nasal airway of the subject.

27. The nasal delivery device of claim 26, wherein the alignment device comprises an optical device generally collinearly aligned with the delivery axis of the aerosolized treatment agent to provide a view into the nostril of the patient to facilitate alignment of the delivery axis of the aerosolized treatment agent with the nasal airway of the subject.

28. The nasal delivery device of claim 27, wherein the optical device comprises an eyepiece at one end and a wide angle lens at another end.

29. The nasal delivery device of claim 27, wherein the eyepiece and the lens are not collinearly arranged.

30. The nasal delivery device of claim 27, wherein the optical device comprises a display screen and a camera.

31. The nasal delivery device of claim 30, wherein the camera is positioned to receive images of an interior of the nostril through the nasal prong.

32. The nasal delivery device of claim 30, wherein the display screen is integrally formed with the nasal delivery device.

33. A method of using the nasal delivery device of claim 1 for delivering the aerosolized treatment agent to the subject, the method comprising:

positioning the nasal prong of the nasal delivery device at least partially within the nostril of the subject;

detecting the oral exhalation of the subject with the remote activation member;

activating the nebulizing device to cause the aerosolization of the treatment agent upon detection of the oral exhalation; and delivering the aerosolized treatment agent through the nasal prong and into the nostril of the subject.

34. The method of claim 33, wherein the act of activating the nebulizing device comprises transmitting an oscillatory force to a surface of a disposable aerosolizing device that contains the treatment agent.

35. The method of claim 33, further comprising directing air from an air flow source through the nasal prong to increase the air flow speed of the aerosolized treatment agent through the nasal prong.

36. The method of claim 33, wherein the act of detecting the oral exhalation comprises detecting a sound generated by air flow associated with the oral exhalation of the subject using a microphone.

37. The method of claim 36, further comprising deflecting air from the oral exhalation towards the microphone.

38. The method of claim 33, further comprising aligning a delivery axis of the aerosolized treatment agent with a nasal airway of the subject.

39. The method of claim 38, wherein the act of aligning the delivery device comprises directing light into the nostril of the subject and detecting light reflected from a surface in the subject's nostril.

40. The method of claim 38, wherein the act of aligning the delivery device comprises directing light into the nostril of the subject and viewing the inside of the nostril using an optical device.

41. The method of claim 40, wherein the act of viewing the inside of the nostril using an optical device comprises displaying an image of the nostril on a display screen.

* * * * *